(12) United States Patent
Byerman et al.

(10) Patent No.: US 7,962,214 B2
(45) Date of Patent: Jun. 14, 2011

(54) NON-SURGICAL DEVICE AND METHODS FOR TRANS-ESOPHAGEAL VAGUS NERVE STIMULATION

(75) Inventors: Bryan P. Byerman, League City, TX (US); Steven E. Maschino, Seabrook, TX (US); Timothy L. Scott, Sugar Land, TX (US)

(73) Assignee: Cyberonics, Inc., Houston, TX (US)

( * ) Notice: Subject to any disclaimer, the term of this patent is extended or adjusted under 35 U.S.C. 154(b) by 514 days.

(21) Appl. No.: 11/829,772

(22) Filed: Jul. 27, 2007

(65) Prior Publication Data

US 2008/0269834 A1 Oct. 30, 2008

Related U.S. Application Data

(63) Continuation-in-part of application No. 11/796,158, filed on Apr. 26, 2007, now Pat. No. 7,869,884.

(51) Int. Cl.
*A61N 1/36* (2006.01)

(52) U.S. Cl. .............. 607/40; 607/1; 607/2; 607/59; 607/115; 607/116; 607/118; 607/133

(58) Field of Classification Search .......... 607/1–2, 607/40, 59, 115–116, 118, 133, 145
See application file for complete search history.

(56) References Cited

U.S. PATENT DOCUMENTS

| | | |
|---|---|---|
| 3,760,812 A | 9/1973 | Timm et al. |
| 3,796,221 A * | 3/1974 | Hagfors .......... 607/59 |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,458,696 A | 7/1984 | Larimore |
| 4,459,989 A | 7/1984 | Borkan |
| 4,503,863 A | 3/1985 | Katims |
| 4,573,481 A | 3/1986 | Bullara |
| 4,590,946 A | 5/1986 | Loeb |
| 4,592,339 A | 6/1986 | Kuzmak et al. |
| 4,608,985 A | 9/1986 | Crish et al. |

(Continued)

FOREIGN PATENT DOCUMENTS

CA 2339971 6/2004

(Continued)

OTHER PUBLICATIONS

PCT International Search Report; PCT/US2008/004469; Nov. 8, 2008.

(Continued)

*Primary Examiner* — Carl H Layno
*Assistant Examiner* — Deborah Malamud
(74) *Attorney, Agent, or Firm* — Chowdhury & Georgakis, P.C.; Jonathan D. Rowell; Timothy L. Scott

(57) ABSTRACT

A method and apparatus for providing trans-esophageal electrical signal therapy to a portion of a vagus nerve of a patient to treat a medical condition. An implantable medical device comprising at least one electrode is implanted in an inner lumen of the esophagus of the patient. At least one electrode is electrically coupled to the inner lumen of the esophagus. An electrical signal from the IMD is provided to a target portion of the vagus nerve through at least a portion of the wall of the esophagus for treating the medical condition.

8 Claims, 24 Drawing Sheets

U.S. PATENT DOCUMENTS

| | | |
|---|---|---|
| 4,612,934 A | 9/1986 | Borkan |
| 4,628,942 A | 12/1986 | Sweeney et al. |
| 4,649,936 A | 3/1987 | Ungar et al. |
| 4,702,254 A | 10/1987 | Zabara |
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |
| 4,969,468 A | 11/1990 | Byers et al. |
| 4,979,511 A | 12/1990 | Terry, Jr. |
| 5,003,975 A | 4/1991 | Hafelfinger et al. |
| 5,025,807 A | 6/1991 | Zabara |
| 5,027,828 A | 7/1991 | Kovacevic et al. |
| 5,074,868 A | 12/1991 | Kuzmak |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,199,430 A | 4/1993 | Fang et al. |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,226,429 A | 7/1993 | Kuzmak |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,351,394 A | 10/1994 | Weinberg |
| 5,354,320 A | 10/1994 | Schaldach et al. |
| 5,411,528 A | 5/1995 | Miller et al. |
| 5,411,531 A | 5/1995 | Hill et al. |
| 5,411,540 A | 5/1995 | Edell et al. |
| 5,423,872 A | 6/1995 | Cigaina |
| 5,458,625 A | 10/1995 | Kendall |
| 5,507,784 A | 4/1996 | Hill et al. |
| 5,514,175 A | 5/1996 | Kim et al. |
| 5,518,001 A | 5/1996 | Snell |
| 5,522,862 A | 6/1996 | Testerman et al. |
| 5,522,865 A | 6/1996 | Schulman et al. |
| 5,531,778 A | 7/1996 | Maschino et al. |
| 5,534,018 A | 7/1996 | Wahlstrand et al. |
| 5,540,730 A * | 7/1996 | Terry et al. ................ 607/40 |
| 5,540,734 A | 7/1996 | Zabara |
| 5,571,150 A | 11/1996 | Wernicke et al. |
| 5,601,604 A | 2/1997 | Vincent |
| 5,601,617 A | 2/1997 | Loeb et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,429 A | 12/1997 | King |
| 5,707,400 A | 1/1998 | Terry, Jr. et al. |
| 5,725,559 A | 3/1998 | Alt et al. |
| 5,743,860 A | 4/1998 | Hively et al. |
| 5,755,750 A | 5/1998 | Petruska et al. |
| 5,771,903 A | 6/1998 | Jakobsson |
| 5,792,210 A | 8/1998 | Wamubu et al. |
| 5,792,212 A | 8/1998 | Weijand |
| 5,814,092 A | 9/1998 | King |
| 5,836,994 A | 11/1998 | Bourgeois |
| 5,861,014 A | 1/1999 | Familoni |
| 5,916,239 A | 6/1999 | Geddes et al. |
| 5,919,216 A | 7/1999 | Houben et al. |
| 5,928,272 A | 7/1999 | Adkins et al. |
| 5,987,352 A | 11/1999 | Klein et al. |
| 5,995,868 A | 11/1999 | Osorio et al. |
| 5,995,872 A | 11/1999 | Bourgeois |
| 6,002,966 A | 12/1999 | Loeb et al. |
| 6,009,877 A | 1/2000 | Edwards |
| 6,026,326 A | 2/2000 | Bardy |
| 6,041,258 A | 3/2000 | Cigaina et al. |
| 6,044,846 A | 4/2000 | Edwards |
| 6,051,017 A | 4/2000 | Loeb et al. |
| 6,073,048 A | 6/2000 | Kieval et al. |
| 6,083,249 A | 7/2000 | Familoni |
| 6,091,992 A | 7/2000 | Bourgeois et al. |
| 6,092,528 A | 7/2000 | Edwards |
| 6,097,984 A * | 8/2000 | Douglas ................ 607/40 |
| 6,101,412 A | 8/2000 | Duhaylongsod |
| 6,102,922 A | 8/2000 | Jakobsson et al. |
| 6,104,955 A | 8/2000 | Bourgeois |
| 6,104,956 A | 8/2000 | Naritoku et al. |
| 6,115,635 A | 9/2000 | Bourgeois |
| 6,129,685 A | 10/2000 | Howard |
| 6,132,361 A | 10/2000 | Epstein et al. |
| 6,141,590 A | 10/2000 | Renirie et al. |
| 6,152,953 A | 11/2000 | Hipskind |
| 6,161,044 A | 12/2000 | Silverstone |
| 6,175,764 B1 | 1/2001 | Loeb et al. |
| 6,181,965 B1 | 1/2001 | Loeb et al. |
| 6,205,359 B1 | 3/2001 | Boveja |
| 6,208,902 B1 | 3/2001 | Boveja |
| 6,214,032 B1 | 4/2001 | Loeb et al. |
| 6,216,039 B1 | 4/2001 | Bourgeois |
| 6,219,580 B1 | 4/2001 | Faltys et al. |
| 6,238,423 B1 | 5/2001 | Bardy |
| 6,243,607 B1 | 6/2001 | Mintchev et al. |
| 6,259,951 B1 | 7/2001 | Kuzma et al. |
| 6,266,564 B1 | 7/2001 | Hill et al. |
| 6,269,270 B1 | 7/2001 | Boveja |
| 6,295,472 B1 | 9/2001 | Rubinstein et al. |
| 6,308,102 B1 | 10/2001 | Sieracki et al. |
| 6,321,124 B1 | 11/2001 | Cigaina |
| 6,327,503 B1 | 12/2001 | Familoni |
| 6,339,725 B1 | 1/2002 | Naritoku et al. |
| 6,341,236 B1 | 1/2002 | Osorio et al. |
| 6,356,786 B1 | 3/2002 | Rezai et al. |
| 6,356,787 B1 | 3/2002 | Rezai et al. |
| 6,356,788 B2 | 3/2002 | Boveja |
| 6,366,813 B1 | 4/2002 | DiLorenzo |
| 6,366,814 B1 | 4/2002 | Boveja |
| 6,374,140 B1 | 4/2002 | Rise |
| 6,381,495 B1 | 4/2002 | Jenkins |
| 6,381,496 B1 | 4/2002 | Meadows et al. |
| 6,381,499 B1 | 4/2002 | Taylor et al. |
| 6,405,732 B1 | 6/2002 | Edwards et al. |
| 6,418,344 B1 | 7/2002 | Rezai et al. |
| 6,418,348 B1 | 7/2002 | Witte |
| 6,425,852 B1 | 7/2002 | Epstein et al. |
| 6,438,423 B1 | 8/2002 | Rezai et al. |
| 6,449,512 B1 | 9/2002 | Boveja |
| 6,450,173 B1 | 9/2002 | Forsell et al. |
| 6,453,199 B1 | 9/2002 | Kobozev |
| 6,459,936 B2 | 10/2002 | Fischell et al. |
| 6,463,328 B1 | 10/2002 | John |
| 6,466,822 B1 | 10/2002 | Pless |
| 6,473,644 B1 | 10/2002 | Terry, Jr. et al. |
| 6,473,652 B1 | 10/2002 | Sarwal et al. |
| 6,473,653 B1 | 10/2002 | Schallhorn et al. |
| 6,477,417 B1 | 11/2002 | Levine |
| 6,477,418 B2 | 11/2002 | Plicchi et al. |
| 6,477,423 B1 | 11/2002 | Jenkins |
| 6,480,743 B1 | 11/2002 | Kirkpatrick et al. |
| 6,484,132 B1 | 11/2002 | Hively et al. |
| 6,487,446 B1 | 11/2002 | Hill et al. |
| 6,505,074 B2 | 1/2003 | Boveja et al. |
| 6,510,332 B1 | 1/2003 | Greenstein |
| 6,522,928 B2 | 2/2003 | Whitehurst et al. |
| 6,532,388 B1 | 3/2003 | Hill et al. |
| 6,535,764 B2 | 3/2003 | Imran et al. |
| 6,542,776 B1 | 4/2003 | Gordon et al. |
| 6,549,804 B1 | 4/2003 | Osorio et al. |
| 6,556,868 B2 | 4/2003 | Naritoku et al. |

| Patent No. | Date | Inventor |
|---|---|---|
| 6,564,101 B1 | 5/2003 | Zikria |
| 6,564,102 B1 | 5/2003 | Boveja |
| 6,567,703 B1 | 5/2003 | Thompson et al. |
| 6,579,280 B1 | 6/2003 | Kovach et al. |
| 6,587,719 B1 | 7/2003 | Barrett et al. |
| 6,587,724 B2 | 7/2003 | Mann |
| 6,587,726 B2 | 7/2003 | Lurie et al. |
| 6,587,727 B2 | 7/2003 | Osorio et al. |
| 6,591,137 B1 | 7/2003 | Fischell et al. |
| 6,591,138 B1 | 7/2003 | Fischell et al. |
| 6,600,953 B2 | 7/2003 | Flesler et al. |
| 6,600,956 B2 | 7/2003 | Maschino et al. |
| 6,606,518 B1 | 8/2003 | Cigaina |
| 6,606,523 B1 | 8/2003 | Jenkins |
| 6,609,025 B2 | 8/2003 | Barrett et al. |
| 6,609,030 B1 | 8/2003 | Rezai et al. |
| 6,609,031 B1 | 8/2003 | Law et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,625,492 B2 | 9/2003 | Florio et al. |
| 6,628,987 B1 | 9/2003 | Hill et al. |
| 6,650,943 B1 | 11/2003 | Whitehurst et al. |
| 6,656,125 B2 | 12/2003 | Misczynski et al. |
| 6,656,960 B2 | 12/2003 | Puskas |
| 6,662,052 B1 | 12/2003 | Sarwal et al. |
| 6,662,053 B2 | 12/2003 | Borkan |
| 6,668,191 B1 | 12/2003 | Boveja |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,681,003 B2 | 1/2004 | Linder et al. |
| 6,684,104 B2 | 1/2004 | Gordon et al. |
| 6,684,105 B2 | 1/2004 | Cohen et al. |
| 6,687,538 B1 | 2/2004 | Hrdlicka et al. |
| 6,690,973 B2 | 2/2004 | Hill et al. |
| 6,690,974 B2 | 2/2004 | Archer et al. |
| 6,708,064 B2 | 3/2004 | Rezai |
| 6,721,603 B2 | 4/2004 | Zabara et al. |
| 6,731,979 B2 | 5/2004 | MacDonald |
| 6,731,986 B2 | 5/2004 | Mann |
| 6,735,474 B1 | 5/2004 | Loeb et al. |
| 6,735,475 B1 | 5/2004 | Whitehurst et al. |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,788,970 B1 | 9/2004 | Park et al. |
| 6,793,670 B2 | 9/2004 | Osorio et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,889,076 B2 | 5/2005 | Cigaina |
| 6,895,278 B1 | 5/2005 | Gordon |
| 6,904,390 B2 | 6/2005 | Nikitin et al. |
| 6,907,295 B2 | 6/2005 | Gross et al. |
| 6,908,487 B2 | 6/2005 | Cigaina |
| 6,920,357 B2 | 7/2005 | Osorio et al. |
| 6,934,580 B1 | 8/2005 | Osorio et al. |
| 6,944,501 B1 | 9/2005 | Pless |
| 6,961,618 B2 | 11/2005 | Osorio et al. |
| 6,990,377 B2 | 1/2006 | Gliner et al. |
| 7,006,859 B1 | 2/2006 | Osorio et al. |
| 7,054,792 B2 | 5/2006 | Frei et al. |
| 7,079,977 B2 | 7/2006 | Osorio et al. |
| 7,139,677 B2 | 11/2006 | Hively et al. |
| 7,146,211 B2 | 12/2006 | Frei et al. |
| 7,149,572 B2 | 12/2006 | Frei et al. |
| 7,167,750 B2 | 1/2007 | Knudson et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,231,254 B2 | 6/2007 | DiLorenzo |
| 7,242,983 B2 | 7/2007 | Frei et al. |
| 7,242,984 B2 | 7/2007 | DiLorenzo |
| 7,263,467 B2 | 8/2007 | Sackellares et al. |
| 7,277,758 B2 | 10/2007 | DiLorenzo |
| 7,280,867 B2 | 10/2007 | Frei et al. |
| 7,282,030 B2 | 10/2007 | Frei et al. |
| 7,295,881 B2 | 11/2007 | Cohen et al. |
| 7,321,837 B2 | 1/2008 | Osorio et al. |
| 7,324,851 B1 | 1/2008 | DiLorenzo |
| 7,340,302 B1 | 3/2008 | Falkenberg et al. |
| 7,346,391 B1 | 3/2008 | Osorio et al. |
| 7,373,199 B2 | 5/2008 | Sackellares et al. |
| 7,389,144 B1 | 6/2008 | Osorio et al. |
| 7,401,008 B2 | 7/2008 | Frei et al. |
| 7,403,820 B2 | 7/2008 | DiLorenzo |
| 2002/0072782 A1 | 6/2002 | Osorio et al. |
| 2002/0099417 A1 | 7/2002 | Naritoku et al. |
| 2003/0074039 A1 | 4/2003 | Puskas |
| 2003/0083716 A1 | 5/2003 | Nicolelis et al. |
| 2003/0181958 A1 | 9/2003 | Dobak |
| 2003/0181959 A1 | 9/2003 | Dobak |
| 2003/0208212 A1 | 11/2003 | Cigaina |
| 2003/0212440 A1 | 11/2003 | Boveja |
| 2003/0236558 A1 | 12/2003 | Whitehurst et al. |
| 2004/0015205 A1 | 1/2004 | Whitehurst et al. |
| 2004/0069330 A1 | 4/2004 | Rolfson |
| 2004/0138517 A1 | 7/2004 | Osorio et al. |
| 2004/0167583 A1 | 8/2004 | Knudson et al. |
| 2004/0172085 A1 | 9/2004 | Knudson et al. |
| 2004/0172088 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0210270 A1 | 10/2004 | Erickson |
| 2004/0210274 A1 | 10/2004 | Bauhahn et al. |
| 2004/0249416 A1 | 12/2004 | Yun et al. |
| 2005/0004621 A1 | 1/2005 | Boveja et al. |
| 2005/0007232 A1 | 1/2005 | Ono et al. |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0038484 A1 | 2/2005 | Knudson et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065562 A1 | 3/2005 | Rezai |
| 2005/0065573 A1 | 3/2005 | Rezai |
| 2005/0065575 A1 | 3/2005 | Dobak |
| 2005/0075691 A1 | 4/2005 | Phillips et al. |
| 2005/0124901 A1 | 6/2005 | Misczynski et al. |
| 2005/0131467 A1 | 6/2005 | Boveja et al. |
| 2005/0131485 A1* | 6/2005 | Knudson et al. ................ 607/40 |
| 2005/0131486 A1 | 6/2005 | Boveja et al. |
| 2005/0131506 A1 | 6/2005 | Rezai et al. |
| 2005/0153885 A1 | 7/2005 | Yun et al. |
| 2005/0154425 A1 | 7/2005 | Boveja et al. |
| 2005/0187590 A1 | 8/2005 | Boveja et al. |
| 2005/0192644 A1 | 9/2005 | Boveja et al. |
| 2005/0209653 A1 | 9/2005 | Herbert et al. |
| 2005/0283200 A1 | 12/2005 | Rezai et al. |
| 2006/0074449 A1 | 4/2006 | Denker et al. |
| 2006/0079936 A1 | 4/2006 | Boveja |
| 2006/0095081 A1 | 5/2006 | Zhou et al. |
| 2006/0111644 A1 | 5/2006 | Guttag et al. |
| 2006/0190056 A1 | 8/2006 | Fowler et al. |
| 2006/0195155 A1 | 8/2006 | Firlik et al. |
| 2006/0200206 A1 | 9/2006 | Firlik et al. |
| 2006/0212091 A1 | 9/2006 | Lozano et al. |
| 2006/0217780 A1 | 9/2006 | Gliner et al. |
| 2006/0224067 A1 | 10/2006 | Giftakis et al. |
| 2006/0224191 A1 | 10/2006 | DiLorenzo |
| 2006/0241697 A1 | 10/2006 | Libbus et al. |

| | | | |
|---|---|---|---|
| 2006/0241725 | A1 | 10/2006 | Libbus et al. |
| 2006/0265021 | A1 | 11/2006 | Herbert et al. |
| 2006/0293720 | A1 | 12/2006 | DiLorenzo |
| 2007/0233192 | A1 | 10/2007 | Craig |
| 2007/0255337 | A1 | 11/2007 | Lu |
| 2008/0269833 | A1 | 10/2008 | Scott et al. |
| 2008/0269840 | A1 | 10/2008 | Scott et al. |

FOREIGN PATENT DOCUMENTS

| | | |
|---|---|---|
| EP | 1070518 | 1/2001 |
| WO | 9639932 | 12/1996 |
| WO | 2004036377 | 4/2004 |
| WO | 2004064918 | 8/2004 |
| WO | 2004069330 | 8/2004 |
| WO | 2005007120 | 1/2005 |
| WO | 2005007232 | 1/2005 |
| WO | 2005067599 | 7/2005 |
| WO | 2006050144 | 5/2006 |
| WO | 2006122148 | 11/2006 |

OTHER PUBLICATIONS

Written Opinion of the International Searching Authority; PCT/US2008/004469; Nov. 8, 2008.

Kriwanek, S., et al.; "Therapeutic Failures After Gastric Bypass Operations Pot Morbid Obesity," Langenbecks Archiv Fur Chirurgie, 38(2): 70-74, 1995.

Grundy et al., "Sensory Afferents From the Gastrointestinal Tract" Chapter 16, Handbook of Physiology of Abdominal Vagal Afferents, Chapter 12, CRC Press, New York, NY, 1992.

Rogers, R., et al. "External Sensory Events and the Control of the Gastrointestinal Tract: An Introduction," Neuroanatomy and Physiology of Abdominal Vagal Afferents, Chapter 5. CRC Press, New York, NY, 1992.

Leibowitz, S.F., "Central Physiological Determinants of Eating Behavior and Weight" Eating Disorders and Obesity: A Comprehensive Handbook.

Woodbury, et al., "Vagal Stimulation Reduces the Severity of Maximal Electroshock Seizures in Intact Rats. Use of a Cuff Electrode for Stimulating and Recording"; Pacing and Clinical Electrophysiology, vol. 14 (Jan. 1991), pp. 94-107.

Zabara, Jacob; "Inhibition of Experimental Seizures in Canines by Repetitive Vagal Stimulation;" Epilepsia, vol. 33 (6) (1992), pp. 1005-1012.

Henry, Thomas R.; "Therapeutic Mechanisms of Vague Name Stimulation;". Neurology, vol. 59 (Supp 4) (Sep. 2002), pp. S3-S14.

Lockard et al., "Feasibility and Safety of Vagal Stimulation in Monkey Model;" Epilepsia, vol. 31 (Supp. 2) (1990), pp. S20-S26.

Hallowitz et al., "Effects of Vagal Volleys on Units of Intralaminar and Juxtalaminar Thalamic Nuclei in Monkeys;" Brain Research, vol. 130 (1977), pp. 271-286.

Bachman, D.,S. et al.; "Effects of Vagal Volleys and Serotonin on Units of Cingulate Cortex in Monkeys;" Brain Research, vol. 130 (1977). pp. 253-269.

Terry et al.; "The Implantable Neurocybernetic Prosthesis System", Pacing and Clinical Electrophysiology, vol. 14, No. 1 (Jan. 1991), pp. 86-93.

Vonck, K., et al. "The Mechanism of Action of Vagus Nerve Stimulation for Refractory Epilepsy—The Current Status", Journal of Neurophysiology, vol. 18 No. 5 (2001), pp. 394-401.

Dietrich, S., et al.; "A Novel Transcutaneous Vagus Nerve Stimulation Leads to Brainstem and Cerebral Activations Measured by Functional MRI;" Biomed Tech 2008, vol. 53, pp. 104-111.

Ritter, S., et al.; "Participation of Vagal Sensory Neurons in Putative Satiety Signals from the Upper Gastrointestinal Tract" Neuroanatomy and Physiology of Abdominal Vagal Afferents, Ch. 10 (1992); pp. 222-248.

* cited by examiner

NON-SURGICAL DEVICE AND METHODS FOR TRANS-ESOPHAGEAL VAGUS NERVE STIMULATION

CROSS-REFERENCE TO RELATED APPLICATION

This application is a Continuation In Part (CIP) of U.S. patent application Ser. No. 11/796,158, now U.S. Pat. No. 7,869,884, entitled "Non-Surgical Device And Methods For Trans-Esophageal Vagus Nerve Stimulation," which was filed on Apr. 26, 2007.

BACKGROUND

1. Technical Field

The subject matter of this disclosure generally relates to the field of medical devices. More specifically, the present disclosure relates to non-surgically implantable medical devices and methods for implementing vagus nerve therapy.

2. Background Information

Many advancements have been made in treating medical conditions involving or mediated by the neurological systems and structures of the human body. In addition to drugs and surgical intervention, therapies using electrical signals for modulating the electrical activity of the body have been found to be effective. In particular, medical devices have been effectively used to deliver therapeutic electrical signals to various portions of a patient's body (e.g., the vagus nerve) for treating a variety of medical conditions. Electrical signal therapy may be applied to a target portion of the body by an implantable medical device (IMD) that is located inside the patient's body or, alternatively, may be applied by devices located external to the body. In addition, some proposed devices include a combination of implanted and external components.

The use of medical devices to provide electrical signal therapy has increased rapidly in recent decades. Such devices include pacemakers and defibrillators, which provide electrical signal therapy to heart tissue, as well as spinal cord stimulators for treatment of pain. In addition, devices have also been approved to provide electrical signal therapy to the vagus nerve (the $10^{th}$ cranial nerve) to treat epilepsy and depression. Additional medical devices for providing electrical signal therapy have been proposed for stimulation of other nerves, such as the sympathetic nerve, the phrenic nerve and the occipital nerve.

The vagus nerve (cranial nerve X) is the longest nerve in the human body. It originates in the brainstem and extends, through the jugular foramen, down below the head, to the abdomen. Branches of the vagus nerve innervate various organs of the body, including the heart, the stomach, the lungs, the kidneys, the pancreas, and the liver. In view of the vagus nerve's many functions, a medical device such as an electrical signal generator has been coupled to a patient's vagus nerve to treat a number of medical conditions. In particular, electrical signal therapy for the vagus nerve, often referred to as vagus nerve stimulation (VNS), has been approved in the United States and elsewhere to treat epilepsy and depression. Application of an electrical signal to the vagus nerve is thought to affect some of its connections to areas in the brain that are prone to seizure activity. Because of the vagus nerve's innervation of the stomach, stimulating the vagus nerve may also be therapeutically beneficial to treating eating disorders such as bulimia nervosa, as well as treating morbid obesity.

Current and proposed VNS treatments have involved surgically coupling electrodes to the left and/or right vagus nerves in the neck. Other treatments involve surgically implanting electrodes to one or more surfaces in the abdomen, such as by laparoscopic surgery through the patient's abdominal wall. Electrical signal therapies in addition to VNS have been proposed to treat eating disorders such as obesity. These techniques include coupling electrodes to the exterior and/or interior of the stomach, duodenum, or intestinal walls. However, all of the aforementioned therapies either do not provide stimulation directed specifically to the vagus nerve, substantially interfere with normal gastrointestinal function, require some type of invasive surgery, or all of the above.

Consequently, there is a need for non-surgical devices and methods for treating medical conditions. There is also a need for providing an easily implanted device that provides little or no interference with normal gastrointestinal function. There is also a need to provide improved methods and devices for vagus nerve stimulation, and to avoid undesired side effects associated with conventional surgical vagus nerve stimulation.

BRIEF SUMMARY

The present invention provides devices and methods for non-surgically providing vagus nerve therapy to treat a variety of medical conditions. Embodiments of an IMD provide electrical stimulation to the vagus nerve through the wall of the esophagus (i.e. trans-esophageally) via a device coupled to the inner surface of the esophagus. Furthermore, implantation of the IMD may be accomplished non-surgically by oral insertion, precluding the need for incisions or even laparoscopic surgery.

In an embodiment, an implantable medical device for providing a therapeutic electrical signal to a vagus nerve of a patient comprises a support member having an outer surface. The support member is adapted to engage the inner wall of an esophagus. The IMD also comprises at least one electrode disposed on the outer surface of the support member. The at least one electrode is adapted to apply a trans-esophageal electrical signal to a vagus nerve through the wall of the esophagus from the inner lumen thereof. The implantable medical device further comprises a signal generator coupled to the support member and to the at least one electrode. The signal generator generates the electrical signal for application to the vagus nerve to treat a medical condition.

In another embodiment, an implantable medical device comprises a support member having an outer surface adapted to engage an inner surface of an esophagus of a patient. The implantable medical device comprises at least one electrode coupled to the outer surface of the support member. The at least one electrode is adapted to apply an electrical signal to a vagus nerve through the wall of the esophagus. Additionally, the implantable medical device comprises a signal generator coupled to the support member and to the at least one electrode. The signal generator is capable of generating an electrical signal for application to a vagus nerve of the patient. Furthermore, the implantable medical device comprises a power supply coupled to said support member and to the signal generator. The power supply is capable of providing electrical power to the signal generator.

In yet another embodiment, a medical device system comprises a support member having an outer surface. The outer surface is adapted to engage an inner surface of an esophagus of a patient. The system also comprises at least one electrode coupled to the outer surface of the support member and adapted to apply a therapeutic electrical signal trans-esophageally to a vagus nerve of the patient. Furthermore, the system comprises a signal generator coupled to the support member and to the at least one electrode. The signal generator is capable of generating said electrical signal for application to a vagus nerve. In addition, the system comprises a power supply for providing electrical power to said signal generator. The system also comprises an external programming system for programming one or more parameters defining said therapeutic electrical signal.

In an embodiment, a method of providing electrical signal therapy to a vagus nerve of a patient comprises implanting a medical device which includes at least one electrode in the lumen of the abdominal portion of the esophagus of the patient such that the at least one electrode is in contact with the surface of the esophagus wall. The method further comprises applying an electrical signal to at least one vagus nerve of the patient through the wall of the esophagus to treat a medical condition of the patient.

In another embodiment, a method of providing electrical signal therapy to a vagus nerve of a patient comprises using an ambulatory medical device to apply an electrical signal trans-esophageally to a vagus nerve of the patient from inside the abdominal portion of an esophagus.

In another embodiment, a method of providing an electrical signal therapy to a vagus nerve of a patient comprises providing an ambulatory medical device, which in turn comprises a support member having an outer surface, at least one electrode on the outer surface of the support member, and an electrical signal generator coupled to the support member and to the at least one electrode. The method further comprises non-surgically implanting the ambulatory medical device, generating a therapeutic electrical signal using the electrical signal generator, and applying the therapeutic electrical signal trans-esophageally to a vagus nerve of a patient from inside the abdominal portion of the patient's esophagus.

In another embodiment of the present invention, a method is provided for providing trans-esophageal electrical signal therapy to a portion of a vagus nerve of a patient to treat a medical condition. An implantable medical device comprising at least one electrode is implanted in an inner lumen of the esophagus of the patient. At least one electrode is electrically coupled to the inner lumen of the esophagus. An electrical signal from the IMD is provided to a target portion of the vagus nerve through at least a portion of the wall of the esophagus for treating the medical condition.

In another embodiment of the present invention, an implantable medical device is provided for providing a trans-esophageal electrical signal therapy to a target portion of a vagus nerve of a patient to treat a medical condition. The implantable medical device includes an outer shell that includes a first surface configured in a substantially low profile shape and a second surface. The second surface for contacting a portion of the inner wall of the esophagus is shaped to conform to an inner wall of the esophagus of a patient. The IMD also includes at least one electrode that protrudes from the outer shell. The at least one electrode is capable of being electrically coupled to a portion of the wall of the esophagus of a patient. The IMD also includes a power supply to provide power for an operation performed by the IMD. The IMD also includes a signal generation unit that is operatively coupled to the power supply. The signal generation unit is adapted to generate an electrical signal to provide a therapeutic electrical signal to a vagus nerve through at least the portion of the wall of the esophagus of the patient.

In yet another embodiment of the present invention, another implantable medical device is provided for providing electrical signal therapy to a portion of a vagus nerve of a patient to treat a disorder. The IMD includes a first member and a second member. The first member is configured to telescopically interface with the second member. The first and second members forming a ring. In one embodiment, the first member is a male member and the second member is a female member. The ring is adapted to direct an outward force to assist the IMD in maintaining a predetermined position within the inner portion of a patient's esophagus. The IMD also includes a power supply that is configured within at least one of the first and second members. The IMD also includes a signal generation unit that is operatively coupled to the power supply. The signal generation unit is adapted to generate an electrical signal to provide stimulation to a vagus nerve through at least a portion of the esophagus wall of the patient. The signal generation unit is configured within the first member or second member. The IMD also includes at least one electrode coupled to at least one of the first and second members. The electrode is adapted to apply the electric signal to the vagus nerve through at least a portion of the wall of the esophagus.

In another embodiment of the present invention, yet another implantable medical device is provided for providing trans-esophageal electrical signal therapy to a portion of a vagus nerve of a patient to treat a medical condition. The IMD includes a first arm and a second arm, each of the arms having a proximal and a distal end. The IMD also includes a first electrode coupled to the distal end of the first arm and a second electrode coupled to the distal end of the second arm. The first and second electrodes are adapted to deliver the electrical signal to a target location of a inner portion of the esophagus. The IMD also includes a main body that is coupled to the proximate end of the first arm and to the proximate end of the second arm. The main body includes a spring mechanism for providing a retaining force upon the first and second arms such that the electrodes are electrically coupled to the target location of the inner portion of the esophagus. The IMD includes a power supply for providing power for an operation performed by the IMD and a signal generation unit that is operatively coupled to the power supply. The signal generation unit is adapted to generate the trans-esophageal electrical signal for application to a portion of the vagus nerve of the patient.

The foregoing has broadly outlined certain features and technical advantages of the invention in order that the detailed description of embodiments of the invention that follows may be better understood. Additional features and advantages of embodiments of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Figure 1:
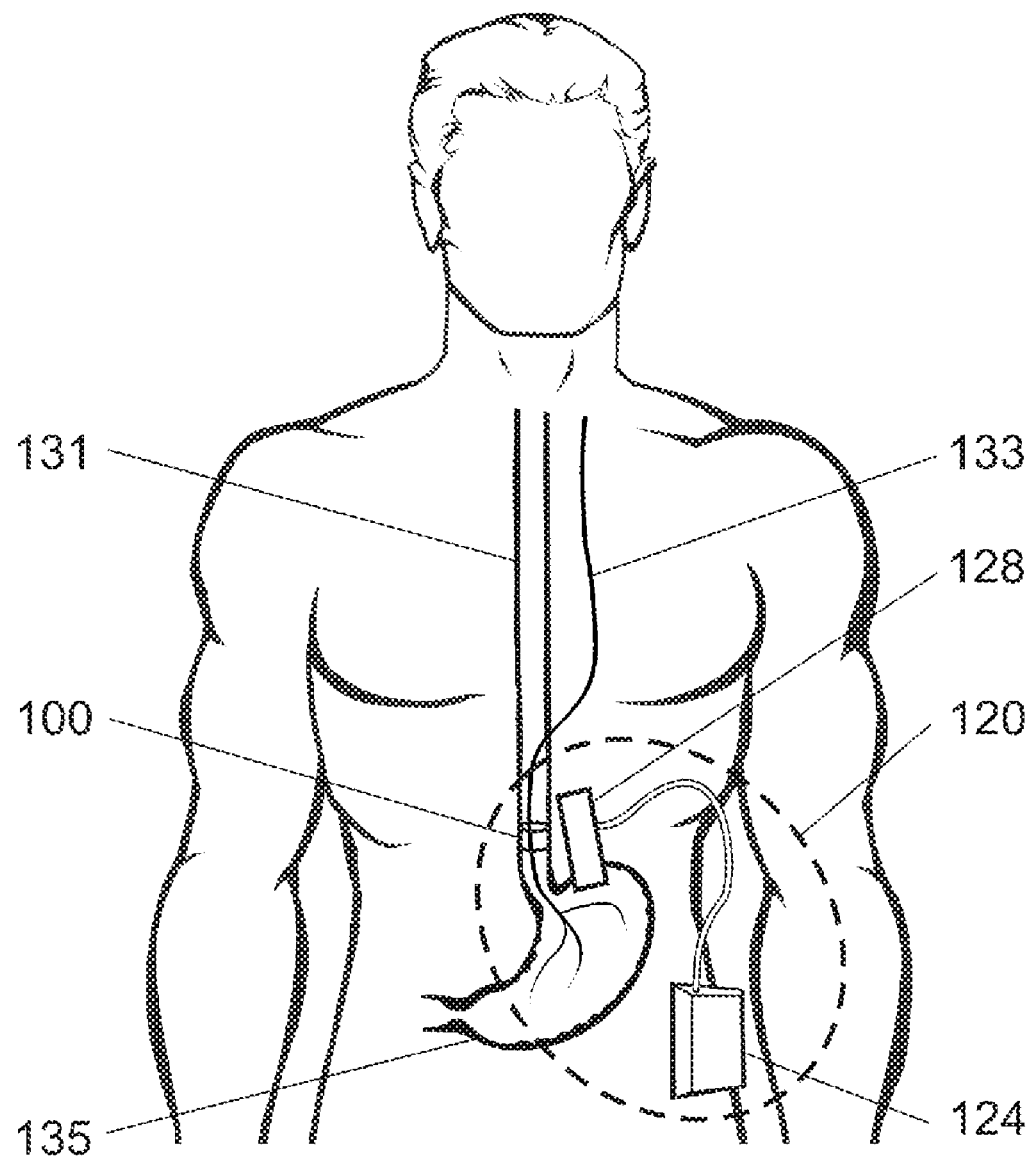
FIG. 1 depicts, in schematic form, an embodiment of an implantable medical device (IMD) system comprising an IMD implanted within a patient and an external device for programming the IMD and, in an alternative embodiment, providing power to the IMD.

Certain terms are used throughout the following description and claims to refer to particular system components. This document does not intend to distinguish between components that differ in name but not function. In the following discussion and in the claims, the terms "including" and "comprising" are used in an open-ended fashion, and thus should be interpreted to mean "including, but not limited to . . .". Also, the term "couple" or "couples" is intended to mean either an indirect or direct electrical connection. Thus, if a first device couples to a second device, that connection may be through a direct electrical connection, or through an indirect electrical connection via other devices and connections.

The term "implantable medical device" refers to any medical device placed inside the human body. The placement of such a device may occur in a body lumen of the patient, such as the esophagus or a blood vessel, or may involve surgical implantation, such as when a conventional VNS system is implanted in the patient's chest and neck area. Furthermore, as defined herein, the term "non-surgical" is used to describe methods that do not require incision or dissection of body tissues to effect implantation of an IMD. In one embodiment, non-surgical implantation may involve placing a medical device in the esophagus of a patient using, e.g., laparoscopic instruments extending from the patient's mouth, through the throat, and into the esophagus.

A "therapeutic signal" refers to a stimulation signal delivered to a patient's body with the intent of treating a medical condition by providing a modulating effect to neural tissue. "Stimulate" or "stimulation signal" refers to the application of an electrical, mechanical, magnetic, electro-magnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

The effect of a stimulation signal on neural activity is termed "modulation"; however, for simplicity, the terms "stimulating" and "modulating", and variants thereof, may be used interchangeably. In general, the application of an exogenous signal to a nerve refers to "stimulation" of the neural structure, while the effects of that signal, if any, on the electrical activity of the neural structure are properly referred to as "modulation."

As defined herein, the term "ambulatory" may describe implantable medical devices, portions of which a patient may carry around with minimal effect or interruption to his or her daily lifestyle.

In some medical devices, electrical neurostimulation may be provided by implanting an electrical device (e.g., a pulse generator) underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may apply a series of electrical pulses to the nerve (e.g., a cranial nerve such as a vagus nerve) periodically, intermittently, or continuously throughout the day, or over another predetermined time interval. This type of stimulation is generally referred to as "passive," "non-feedback," or "prophylactic," stimulation. The electrical signal may be applied by an IMD that is implanted within the patient's body. In other cases, the signal may be generated by an external pulse generator outside the patient's body, coupled by an RF or wireless link to an implanted electrode.

Generally, neurostimulation signals that perform neuro-modulation are delivered by the IMD via one or more leads. The leads generally terminate at their distal ends in one or more electrodes, and the electrodes, in turn, are electrically coupled to tissue in the patient's body. For example, a number of electrodes may be attached to various points of a nerve or other tissue inside a human body for delivery of a neurostimulation signal. In some types of neurostimulation devices, electrodes are coupled to the electrical signal generator without the use of leads. In the present invention, some embodiments include leads and some embodiments do not incorporate leads.

While feedback stimulation schemes have been proposed, conventional vagus nerve stimulation (VNS) usually involves non-feedback stimulation characterized by a number of parameters. Specifically, convention vagus nerve stimulation usually involves a series of electrical pulses in bursts defined by an "on-time" and an "off-time." During the on-time, electrical pulses of a defined electrical current (e.g., 0.5-2.0 milliamps) and pulse width (e.g., 0.25-1.0 milliseconds) are delivered at a defined frequency (e.g., 20-30 Hz) for the on-time duration, usually a specific number of seconds, e.g., 10-100 seconds. The pulse bursts are separated from one another by the off-time, (e.g., 30 seconds-5 minutes) in which no electrical signal is applied to the nerve. The on-time and off-time parameters together define a duty cycle, which is the ratio of the on-time to the combination of the on-time and off-time, and which describes the percentage of time that the electrical signal is applied to the nerve.

In conventional VNS, the on-time and off-time may be programmed to define an intermittent pattern in which a repeating series of electrical pulse bursts are generated and applied to the vagus nerve. Each sequence of pulses during an on-time may be referred to as a "pulse burst." The burst is followed by the off-time period in which no signals are applied to the nerve. The off-time is provided to allow the nerve to recover from the stimulation of the pulse burst, and to conserve power. If the off-time is set at zero, the electrical signal in conventional VNS may provide continuous stimulation to the vagus nerve. Alternatively, the idle time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in conventional VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-150 Hz (i.e., 20 pulses per second to 150 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

DETAILED DESCRIPTION OF THE EMBODIMENTS

The disclosed systems, devices and methods are susceptible to implementation in various embodiments. The disclosure of specific embodiments, including preferred embodiments, is not intended to limit the scope of the invention as claimed unless expressly specified. In addition, persons skilled in the art will understand that the invention has broad application. Accordingly, the discussion of particular embodiments is meant only to be exemplary, and does not imply that the scope of the disclosure, including the claims, is limited to specifically disclosed embodiments.

In some embodiments of the present invention, an implantable medical device may be implanted within a patient's body without surgery. The IMD generates and applies an electrical signal to the vagus nerve of the patient to treat a medical condition. The invention is possible because of the unique anatomy of the left and right vagus nerves. From the neck region, the left vagus nerve rotates anteriorly and becomes attached to the exterior surface of the abdominal or lower esophagus (i.e. the abdominal portion of the esophagus) as the anterior vagus nerve. As used herein, "abdominal esophagus" and "lower esophagus" may be used interchangeably to refer to the portion of the esophagus running from the thorax to the esophagogastric junction of a patient. The right vagus nerve, on the other hand, rotates posteriorly and becomes attached to the exterior surface of the lower esophagus as the posterior vagus nerve. As the anterior and posterior vagus nerves travel down the esophagus, the nerves separate into a number of branches at the esophagus/stomach junction, and the branches remain attached to the outer wall of the stomach. The close proximity of the nerves to the surfaces of the abdominal esophagus and the stomach permit the application of an electrical signal to the vagus nerve from the interior of the abdominal esophagus using a medical device coupled to the esophagus's interior wall.

In alternative embodiments, the invention may include devices and methods for providing electrical signal therapy across the wall of the upper portion of the stomach rather than the abdominal portion of the esophagus. However, the greater accessibility of the vagus nerves at the lower esophagus/stomach junction makes delivery of the signal across the wall of the lower esophagus a preferred embodiment. Application of a therapeutic electrical signal to the stomach is more difficult than the esophagus for a number of reasons. First, the motility of the esophagus is less than that of the stomach, thus making the esophagus a more stable structure. Second, the anterior and posterior vagus nerves are essentially a unitary structure (i.e., a single nerve bundle—albeit with thousands of individual nerve fibers within it—traveling down the length of the lower esophagus), with limited branching until passing onto the surface of the stomach. Accordingly, stimulation of the vagus at the lower esophagus level facilitates modulation of a larger population of nerves than stimulation of only some of the vagus nerve branches on the upper portion of the stomach.

In one embodiment, an ambulatory implantable medical device may be non-surgically implanted within the abdominal esophagus of a patient to deliver an electrical signal to at least one of the anterior or posterior vagus nerves through the wall of the esophagus.

Figure 2:
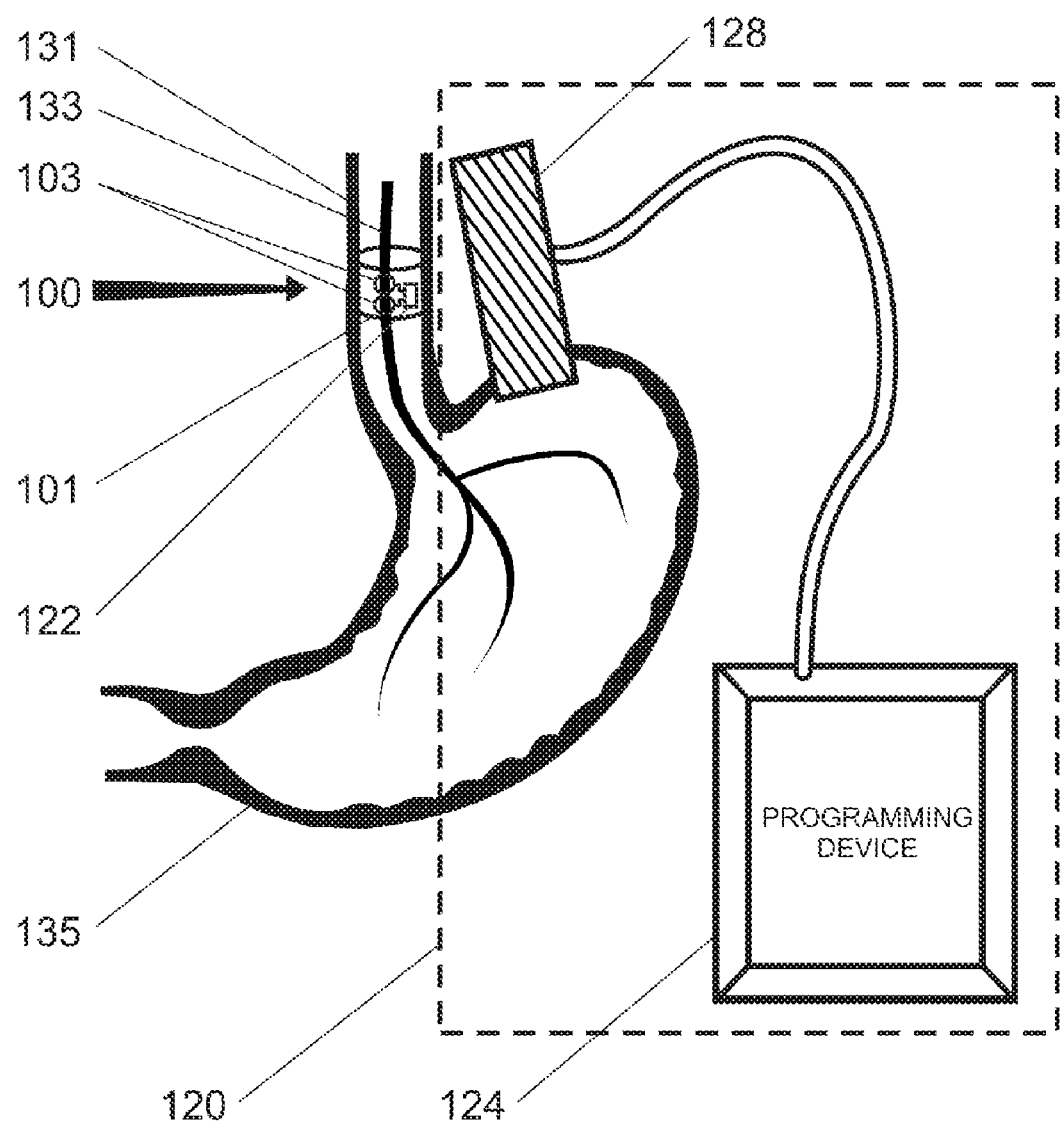
FIG. 2 illustrates an enlarged view of an embodiment of the IMD implanted inside the abdominal portion of the esophagus.

FIGS. 1 and 2 depict an IMD 100 implanted in a patient. In one embodiment, IMD 100 comprises a support member 101. Support member 101 comprises a flexible, biocompatible material and is adapted to be coupled to the inner wall of the lower esophagus of the patient. Moreover, support member 101 has one or more electrodes 103 coupled to its outer surface. An electrical signal generator 122 generates a therapeutic electrical signal to apply to the vagus nerve 133. Signal generator 122 is electrically coupled to electrodes 103. In some embodiments, the electrodes 103 are coupled to the electrical signal generator 122 by leads, while in alternative embodiments the electrodes are directly connected to the electrical signal generator without the use of leads. In addition, programming system 120 may be coupled to electrical signal generator 122. Programming system 120 may generally control and monitor IMD 100 from outside the body as IMD 100 provides stimulation to the vagus nerve to provide therapy to a patient.

In one embodiment, the support member 101 has at least one unipolar electrode coupled to its outer surface. In another embodiment, the support member 101 has a plurality of unipolar electrodes on its outer surface. The plurality of electrodes may include a first plurality on a first side of the support member 101, and a second plurality on a second side of the support member 101. The first plurality may be adapted to provide a trans-esophageal therapeutic electrical signal to an anterior vagus nerve of the patient, and the second plurality of electrodes may be adapted to provide a trans-esophageal therapeutic electrical signal (which may be the same as or different from the signal provided by the first plurality) to a posterior vagus nerve of the patient. Electrodes 103 are used to apply an electrical signal to the vagus nerve 133 through the wall of the lower esophagus 131. In one embodiment, the electrodes 103 contact or engage the inner wall of the esophagus 131. In another embodiment, the electrodes are adapted to partially penetrate the wall of the lower esophagus 131. In a still further embodiment, the electrodes are adapted to completely penetrate the wall of the lower esophagus 131, and in yet another embodiment, the electrodes may comprise multiple electrode elements, some of which contact the inner wall of the esophagus, some of which partially penetrate the esophagus wall, and some of which completely penetrate the wall. Without being bound by theory, it is believed that greater penetration of the wall of the esophagus corresponds with more efficient stimulation of the vagus nerve on the outer wall of the esophagus, since the signal from electrode penetrating the wall in whole or in part will be less attenuated than a signal from electrodes that contact the inner wall of the esophagus without penetration of the same.

In one embodiment, support member 101 has at least one electrode pair (e.g., a cathode and an anode) coupled to its outer surface. In another embodiment, support member 101 has a plurality of electrode pairs on its outer surface. In a further embodiment, support member 101 has at least one unipolar electrode as well as at least one electrode pair on its outer surface. In general, the disposition of electrodes (whether unipolar, bipolar, or a combination of unipolar and bipolar electrodes) may be used to steer the electrical current of the therapeutic electrical signal to effectively modulate the anterior and/or posterior vagus nerves of the patient.

IMD 100 is preferably implanted non-surgically, as described below in more detail. However, in general, IMD 100 is implanted in the lower or abdominal portion of the esophagus via oral insertion of the IMD 100 through the patient's mouth and passage through the throat and the upper esophagus. Since IMD 100 is implanted within the lower esophagus, no incisions are necessary to position the IMD 100 at the desired implantation site. The IMD 100 may be retained in place and migration prevented by suitable anchors to engage the tissue of the esophagus 131. The anchors may comprise any of a number of medical anchors known in the art, e.g., sutures, barbs, staples, adhesives, pins, etc. The IMD 100 may further comprise a retainment element to facilitate maintaining the device in position in the esophagus and to prevent migration. In one embodiment, the support member 101 comprises a ring or partial ring structure with a retainment element comprising a resilient spring made of metal or other suitable material. The resilient spring may be embedded in or coupled to support member 101 (e.g., by mechanical affixation). Support member 101 ring or partial ring may be sized to be slightly larger than the diameter of the patient's esophagus, such that the resilient spring retainment element coupled thereto provides a radially outwardly directed force against the lower esophagus to maintain the device in a fixed position in the esophagus, while allowing the IMD 100 to flex with normal movement of the esophagus.

Once implanted, IMD 100 provides therapy to the patient by generating and applying an electrical signal to the vagus nerve across the wall of the esophagus 131. As used herein, the terms "trans-esophageal" or "trans-esophageally" refer to or describe delivery of a therapy (i.e. vagus nerve stimulation) across the esophageal wall. The signal preferably comprises an electronic signal generated by the electronic signal generator 122 in the inner lumen of the esophagus and applied trans-esophageally to the vagus nerve on the outer surface of the esophagus wall. The electrical signal provided by the electronic signal generator 122 may be defined by programming system 120. In some embodiments, the patient may control and/or alter the therapy by a user signal, e.g., a magnet, a tap sensor, or a patient module for non-invasively transmitting and/or receiving data from the IMD 100, e.g., by RF signals.

Generally, as mentioned above, neurostimulation signals that perform neuromodulation are delivered by the IMD 100 via one or more electrodes 103 as shown in FIG. 2. The modulating effect of the neurostimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in neuro-plasticity or neurogenesis of brain tissue.

Figure 3:
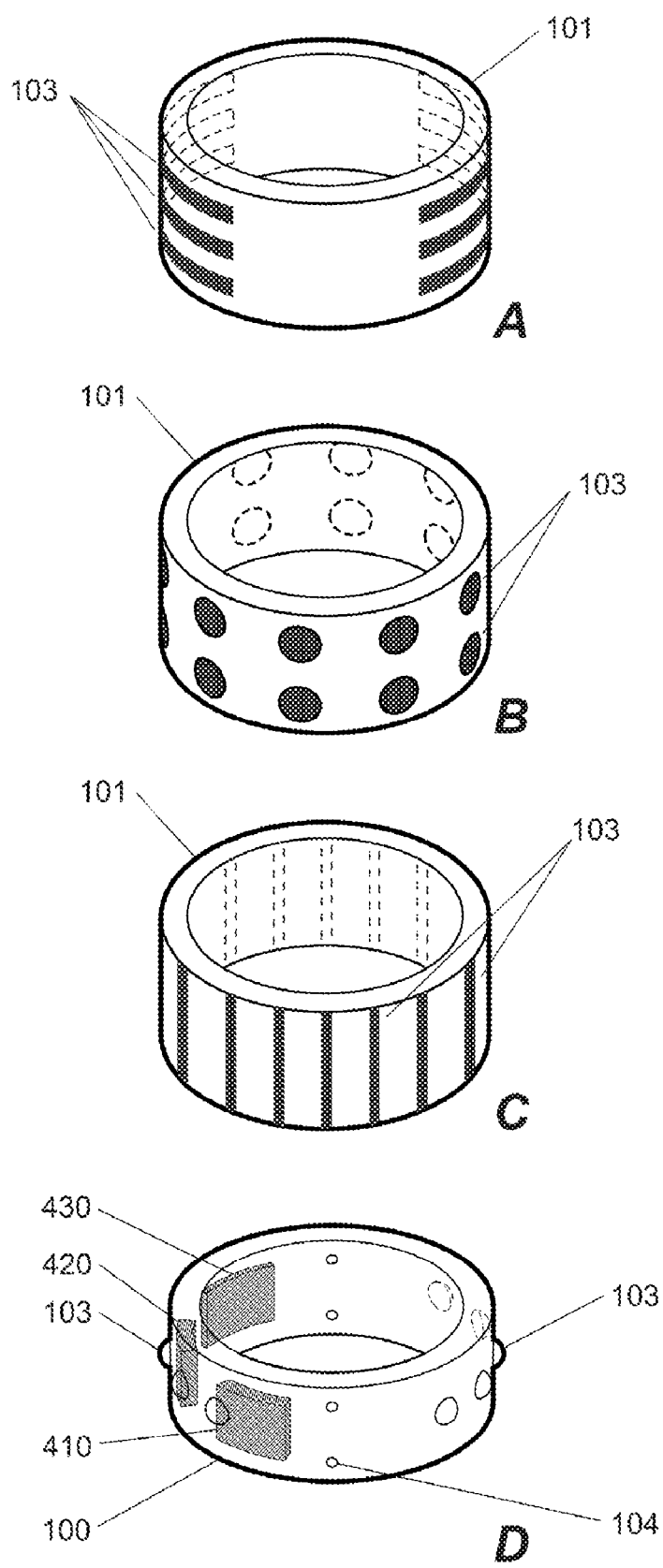
FIGS. 3A-D illustrate embodiments of an IMD according to the present invention.
Figure 5:
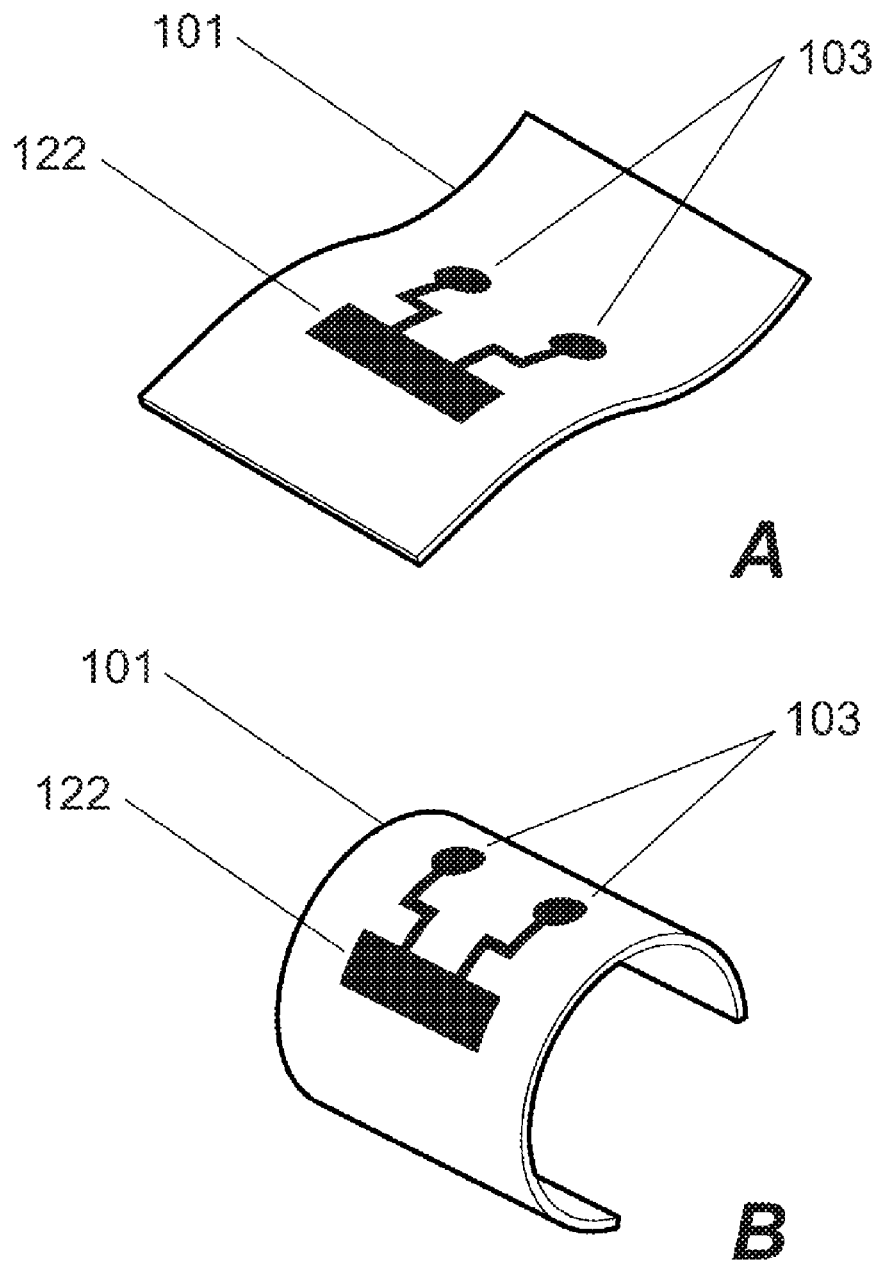
FIGS. 5A-B illustrate embodiments of implantable medical devices according to the present invention.

In a preferred embodiment, the support member 101 is a ring-shaped or tube-shaped member defining a circular cross-section as shown in FIG. 3. The diameter of the support member 101 may be sized to match or slightly exceed the diameter of the esophagus 131. Alternatively, support member 101 may be semi-circular, i.e., comprising an incomplete circle or a C-shape as shown in FIG. 5B. More generally, support member 102 may be of any suitable geometry that conforms to at least a portion of the inner surface of an organ.

Referring to FIG. 5A, in one embodiment, the support member 101 comprises a generally planar, flexible member that is capable of bending to conform to a portion of the inner wall of the lower esophagus 131. In such an embodiment, support member 101 may be comprised of a biocompatible polymer such as silicone rubber in a suitable shape, i.e., a circular shape, a rectangular shape, or any desired shape, and may have an electrical signal generator 122 coupled thereto (for example by embedding the electrical signal generator in the biocompatible polymer). Furthermore, in such an embodiment, support member 101 may be attached to inner wall of esophagus by using a tissue adhesive or biocompatible glue.

In another embodiment, the support member may include a retainment element comprising an expandable stent, which may be introduced into the lumen of the esophagus 131 in a compressed state via conventional balloon catheters, and then expanded by inflating the balloon to conform the device to the size of the esophagus.

According to another embodiment of the invention, the support member 101 has a contracted position to facilitate introduction and implantation of the device in the esophagus, and an expanded position engaging the inner wall of the esophagus to maintain the device in position and reduce or eliminate migration. In one aspect, the support member 101 has a fixed expanded position to hold the device in place within the esophagus. As described in detail above, support member 101 may comprise a retainment element that may be a resilient spring member or a stent to provide a radially outwardly directed force against the inner wall of the esophagus. In addition, support member 101 and the retainment element may be mounted on a catheter in the first, contracted position to facilitate introduction of the IMD 100 into the patient's mouth and passage through the upper esophagus into the lower esophagus, whereupon the IMD 100 may be deployed in the expanded position and optionally further retained in position with one or more anchor members.

In one embodiment, support member 101 may further comprise one or more anchor members (not shown) for attaching the IMD 100 to the inner wall of the esophagus 131. For example, support member 101 may comprise a plurality of suture elements such as a suture ring or apertures so that a surgeon may suture the IMD 100 to the inner esophageal wall to prevent displacement of the IMD 100. In another aspect, the anchor members may comprise a plurality of barbs or protrusions which are capable of grasping or engaging the inner surface of the esophagus, and/or of penetrating the wall of the esophagus, to prevent movement or displacement. The barbs or protrusions may be disposed in close proximity to the electrodes 103 so as to stabilize the IMD 100 in a fixed position relative to the anterior and/or posterior vagus nerves. In a further embodiment, the electrodes 103 may serve as anchor members. For example, electrodes 103 themselves may comprise protrusions which project radially from the support member 101 to engage the wall of the esophagus 131. The electrodes 103 may contact the inner surface of the esophagus wall, and/or may comprise barbs to penetrate the wall in whole or part. Another means of engaging the inner wall of the esophagus comprises a tissue adhesive or biocompatible glue coated on to the outer surface of support member 101.

The support member 101 may be made of any suitable biocompatible material. The materials used in fabricating the IMD 100 are preferably non-toxic such that if the IMD 100 is dislodged into the stomach, it may easily pass through the digestive system. In a preferred embodiment, support member 101 is made of a resilient or flexible biocompatible material such as a polymer. Suitable polymers include without limitation, hydrogels, silicone, polyethylene, polypropylene, polyurethane, polycaprolactone, polytetrafluoroethylene (PTFE), copolymers and combinations of the foregoing, and the like. In another embodiment, the support member is made of a silicone polymer. In alternative embodiments, support member 101 is made of biocompatible metals such as without limitation, titanium, silver, gold, alloys, nitinol, shape-memory metals, or combinations thereof. Furthermore, support member 101 may be made of biological materials such as tissue-engineered esophageal tissue from an animal donor, bovine pericardium, and the like. Where human or animal tissue from a donor is used, the materials are preferably decellularized and cross-linked to minimize adverse immunological reactions and prevent the immune system of the patient from degrading the materials.

Figure 6:
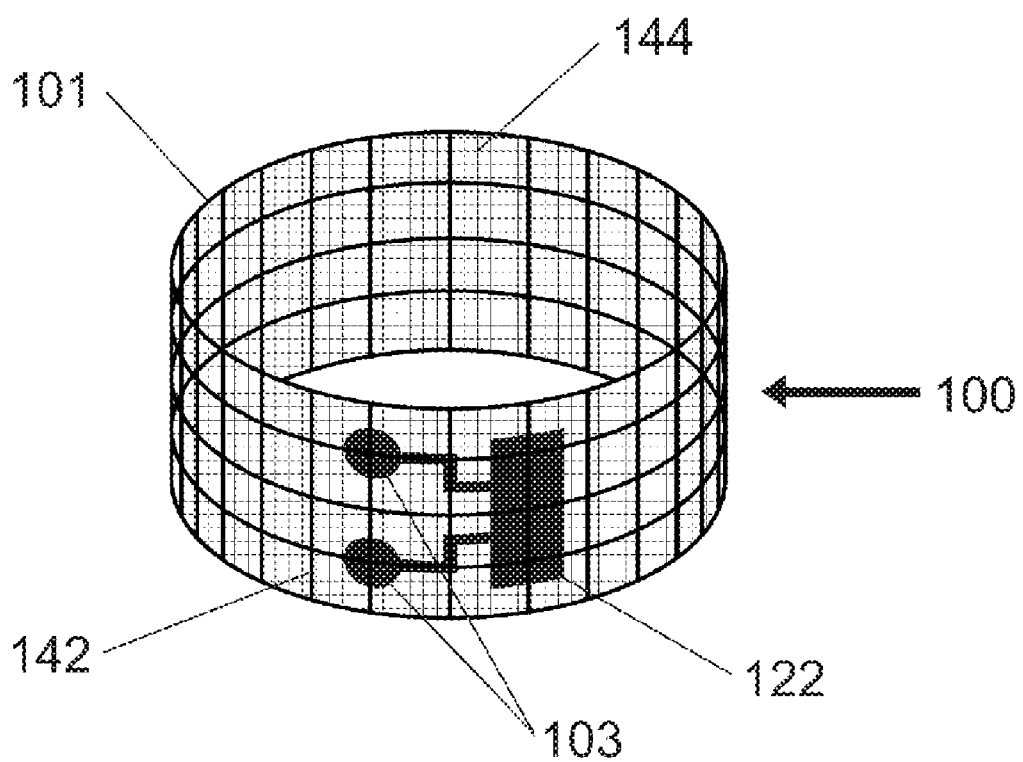
FIG. 6 illustrates an embodiment of an IMD according to the present invention.

FIG. 6 illustrates an embodiment of an IMD 100. IMD 100 may comprise a retainment element 142 comprising a skeleton or frame embedded within a support member 101. The support member may in some embodiments comprise a polymer exterior or coating 144 (e.g., a fabric exterior or engineered polymer to provide improved biocompatibility). The retainment element 142 (depicted in a grid-like configuration although many other geometries may be employed) may be made of a flexible metal or polymer, and has sufficient stiffness when support member 101 is in an expanded position to maintain the position of the IMD 100 in the esophagus. The support member 101 serves as a substrate to which to mount the electrodes 103 and other components of the IMD 100 (e.g., a pulse generator and a controller). In a specific embodiment, the exterior/coating 144 comprises a fatty acid derivative covalently bonded to a silicone polymer comprising the support member 101.

According to an embodiment, when the support member 101 and the retainment element 142 are expanded, they typically have a diameter or size that corresponds to the inner dimensions of the esophagus. For example, the esophagus has an inner diameter ranging from approximately 10 mm to approximately 30 mm. As such, in an embodiment, the support member 101 has an expanded size ranging from approximately 8 mm to about 50 mm, preferably from about 10 mm to about 40 mm, more preferably from about 10 mm to about 35 mm in diameter. In other embodiments, different support members 101 may be fabricated with different sizes such that a surgeon may have the option of selecting the most appropriate size depending on the patient.

The exterior or outer surface of the support member 101 comprises one or more electrodes 103 which apply a therapeutic electrical signal to the wall of the lower esophagus 131. As noted, in alternative embodiments the electrodes 103 may provide an electrical signal therapy across the wall of the upper portion of the stomach instead of or in addition to the lower portion of the esophagus. At any rate, electrodes 103 are disposed on support member 101 such that they will be in close proximity to the vagus nerve when the IMD 100 is non-surgically implanted in the esophagus. Preferably, the electrodes comprise a conductive material such as platinum, iridium, platinum-iridium alloys, gold, silver, copper, aluminum, and/or oxides of the foregoing. The electrodes 103 may be arranged in any suitable pattern on the exterior of the ring. The pattern is preferably optimized to deliver electrical stimulation to the anterior and/or posterior vagus nerves regardless of the location of the IMD 100 within the esophagus. According to one embodiment, electrodes 103 are arranged as parallel bands or rings around all or part of the outer surface of the IMD 100 as shown in FIG. 3A. In another embodiment, electrodes 103 are arranged as rows of circular or hemispherical contacts as shown in FIGS. 3B and 3D, respectively. In still another embodiment, electrodes 103 are arranged in vertical columns of electrodes, with each column acting as a unipolar electrode, a cathode or an anode (FIG. 3C). FIG. 3D also depicts other components of the IMD 100 embedded in support member 101, including a power supply 430, a signal generation unit 420, and a controller 410, as more fully discussed with regard to FIG. 4, below. In some embodiments, apertures 104 may be provided as shown in FIG. 3D for use in conjunction with an anchor member (not shown) such as a suture, barb, pin, etc. This may facilitate modulation of the vagus nerve if rows of electrodes are placed on either side of the descending vagus nerve bundle(s).

Figure 4:
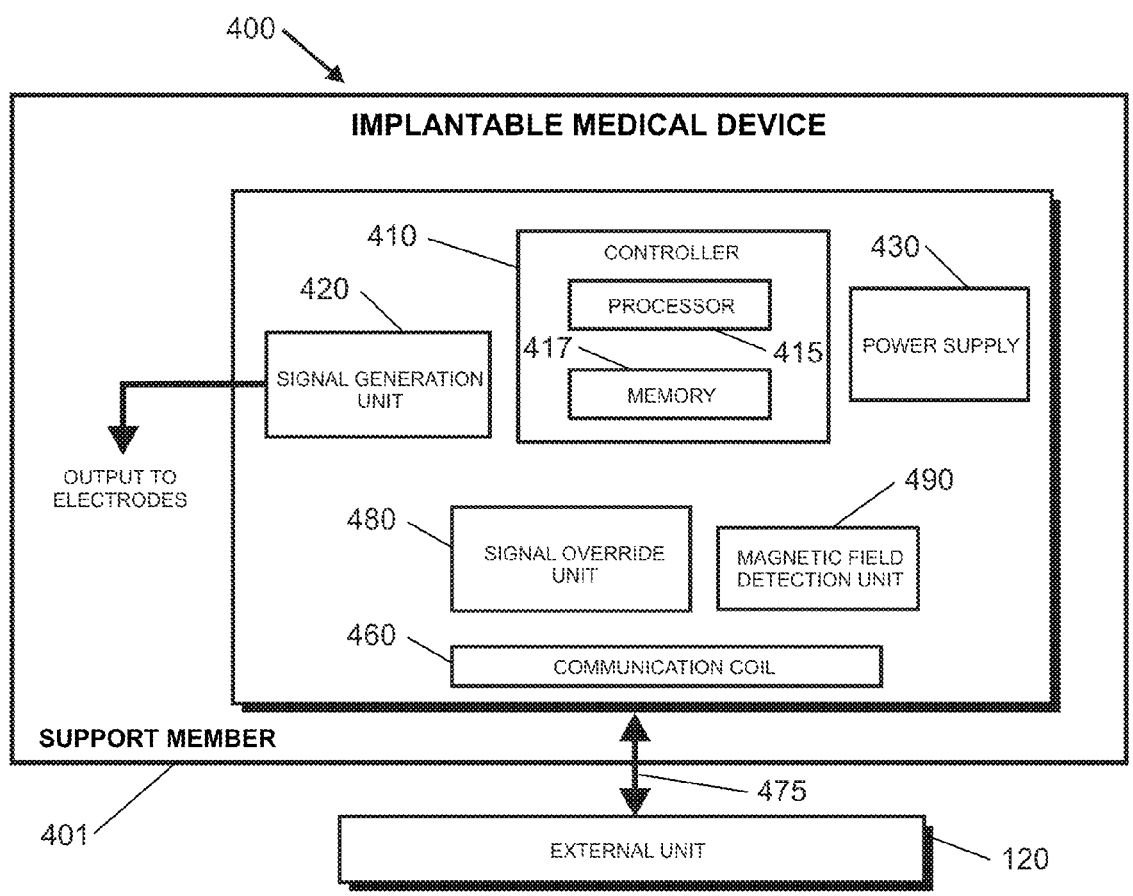
FIG. 4 is a block diagram of an IMD for use in an embodiment of the present invention, and an external unit for communication and programming of the IMD.

FIG. 4 illustrates a block diagram depiction of the IMD 400 of FIG. 1, in accordance with one illustrative embodiment of the present invention. The IMD 400 may be used for electrical signal therapy to treat various disorders, such as (without limitation) epilepsy, depression, bulimia, heart rhythm disorders, gastric-related disorder, a hormonal disorder, a reproductive disorder, a metabolic disorder, a hearing disorder, and/or a pain disorder. The IMD 400 may be coupled to various leads, if necessary, and one or more electrodes for applying a therapeutic electrical signal to an anterior and/or posterior vagus nerve of the patient. Therapeutic electrical signals may be transmitted from the IMD 400 to a lower esophagus wall of the patient, and across the wall of the esophagus to the patient. The electrodes may be positioned either in contact with the inner wall of the esophagus, or may penetrate the wall of the esophagus in whole or in part. The net effect of the IMD 400 and the electrodes is to generate an electrical signal in the inner lumen of the esophagus and to transmit that signal from the inner lumen to a vagus nerve located outside the wall of the esophagus. Therapeutic electrical signals from the IMD 400 may be generated by a signal generation unit 420 and transmitted to the electrode(s) either directly or via one or more leads (not shown). Further, signals from sensor electrodes, which may also have corresponding leads, may also be coupled to the IMD 400. In one embodiment, the electrodes applying the signal to the vagus nerve may also function as sensing electrodes. Sensing electrodes may be used to trigger feedback stimulation routines based upon, e.g., body temperature, EEG recordings, heart rate, vagus nerve activity, etc.

The IMD 400 may comprise a controller 410 capable of controlling various aspects of the operation of the IMD 400. The controller 410 is capable of receiving internal data and/or external data and controlling the generation and delivery of a therapeutic electrical signal to a vagus nerve of the patient's body. For example, the controller 410 may receive manual instructions from an operator externally, or may generate and apply a therapeutic electrical signal based on internal calculations and programming. The controller 410 is capable of affecting substantially all functions of the IMD 400.

The controller 410 may comprise various components, such as a processor 415, a memory 417, etc. The processor 415 may comprise one or more microcontrollers, microprocessors, etc., that are capable of executing a variety of software components. The memory 417 may comprise various memory portions, where a number of types of data (e.g., internal data, external data instructions, software codes, status data, diagnostic data, etc.) may be stored. The memory 417 may store various tables or other database content that could be used by the IMD 400 to implement the override of normal operations. The memory 417 may comprise random access memory (RAM) dynamic random access memory (DRAM), electrically erasable programmable read-only memory (EEPROM), flash memory, etc.

The IMD 400 may also comprise a signal generation unit or pulse generator 420. The signal generation unit 420 is capable of generating and delivering a variety of electrical neurostimulation signals to one or more electrodes, e.g., via leads. The signal generation unit 420 is capable of generating a therapy portion, a ramping-up portion, and a ramping-down portion of the therapeutic electrical signal. In one embodiment, a number of leads may be used to electrically couple the one or more electrodes to the IMD 400. In another embodiment, the electrodes may be directly coupled to the signal generation unit 420. The therapeutic electrical signal may be delivered to the electrodes by the signal generation unit 420 based upon instructions from the controller 410. The signal generation unit 420 may comprise various types of circuitry, such as pulse generators, impedance control circuitry to control the impedance "seen" by the leads, and other circuitry that receives instructions relating to the type of electrical signal therapy to be provided to the patient. The signal generation unit 420 is capable of delivering a controlled current therapeutic electrical signal to the electrodes.

The IMD 400 may also comprise a power supply 430. The power supply 430 may comprise a battery, voltage regulators, capacitors, etc., to provide power for the operation of the IMD 400, including delivering the therapeutic electrical signal. The power supply 430 provides power for the operation of the IMD 400, including electronic operations and the electrical signal function. The power supply is typically a battery. The power supply 430 may comprise a lithium/thionyl chloride cell or a lithium/carbon monofluoride cell. Other battery types known in the art of implantable medical devices may also be used. Any suitable batteries may be used including without limitation, lithium ion, nickel cadmium alkaline, and the like. In a preferred embodiment, the power supply comprises a battery located inside support member 401 and coupled to the pulse generator 420. In an alternative embodiment, the power supply is rechargeable. In one aspect, the power supply may be wirelessly rechargeable. A wirelessly rechargeable power supply may include an external power supply on the outside of the patient's body, inductively coupled to an implanted rectifier and/or capacitor attached to the support member 401. Such a power supply may be charged from outside the patient's body without requiring removal of the medical device. In an alternative embodiment, the power supply 430 may comprise a power converter to convert energy from the patient's body into electrical power for the IMD 400. The converter may use a temperature difference within the patient's body or between the patient's body and the environment to generate electrical power, or may convert body movement (e.g., gastric motility movement, arm movement, or leg movement) into electrical energy to provide power to the IMD 400. In another embodiment, an external power supply may be part of an external unit 120 as will be described below.

The IMD 400 also comprises a communication unit 460 capable of facilitating communications between the IMD 400 and various devices. In particular, the communication unit 460 is capable of providing transmission and reception of electronic signals to and from an external unit 120. In particular, communication unit 460 may be a wireless device capable of transmitting and receiving signals to and from IMD 400 without the use of wires. In some embodiments, the controller 410 and signal generator 420 may be part of an external unit or programming system 120, described in more detail below.

The external unit 120 may be a device that is capable of programming various modules and electrical signal parameters of the IMD 400. In one embodiment, the external unit 120 comprises a computer system that is capable of executing a data-acquisition program. The external unit 120 may be controlled by a healthcare provider, such as a physician, at a base station in, for example, a doctor's office. The external unit 120 may be a computer, preferably a handheld computer or PDA, but may alternatively comprise any other device that is capable of electronic communications and programming. The external unit 120 may download various parameters and program software into the IMD 400 for programming the operation of the implantable device. The external unit 120 may also receive and upload various status conditions and other data from the IMD 400. The communication unit 460 may be hardware, software, firmware, and/or any combination thereof. Communications between the external unit 120 and the communication unit 460 may occur via a wireless or other type of communication, illustrated generally by line 475 in FIG. 4.

The IMD 400 is capable of delivering a therapeutic electrical signal that can be intermittent, periodic, random, sequential, coded, and/or patterned. The electrical signals may comprise an electrical signal frequency of approximately 0.1 to 1000 Hz. The electrical signals may comprise a pulse width of in the range of approximately 1-2000 microseconds. The electrical signals may comprise current amplitude in the range of approximately 0.1 mA to 10 mA. The therapeutic electrical signal may be delivered through either bipolar electrodes (i.e., a cathode (−) electrode and an anode (+) electrode), or may be delivered through one or more unipolar electrodes. In one embodiment, the various blocks illustrated in FIG. 4 may comprise a software unit, a firmware unit, a hardware unit, and/or any combination thereof.

The IMD 400 may also comprise a magnetic field detection unit 490. The magnetic field detection unit 490 is capable of detecting magnetic and/or electromagnetic fields of a predetermined magnitude. Whether the magnetic field results from a magnet placed proximate to the IMD 400, or whether it results from a substantial magnetic field encompassing an area (such as an MRI machine), the magnetic field detection unit 490 is capable of informing the IMD of the existence of a magnetic field.

The magnetic field detection unit 490 may comprise various sensors, such as a Reed Switch circuitry, a Hall Effect sensor circuitry, and/or the like. The magnetic field detection unit 490 may also comprise various registers and/or data transceiver circuits that are capable of sending signals that are indicative of various magnetic fields, the time period of such fields, etc. In this manner, the magnetic field detection unit 490 is capable of deciphering whether the detected magnetic field relates to an inhibitory input or an excitatory input from an external source. The inhibitory input may refer to inhibition of, or deviation from, normal signal generation operation. The excitatory input may refer to additional electrical signal therapy or deviation from normal electrical signal therapy.

The IMD 400 may also include an electrical signal override unit 480. The electrical signal override unit 480 is capable of overriding the reaction by the IMD to the detection of a magnetic signal provided by the magnetic field detection unit 490. The electrical signal override unit 480 may comprise various software, hardware, and/or firmware units that are capable of determining an amount of time period in which to override the detection of a magnetic field. The signal override unit 480 may also contain safety features, such as returning to normal operation despite an override command after a predetermined period of time. The electrical signal override unit 480 is capable of preventing false interruption of normal operation due to false magnetic input signals or unintended magnetic input signals. The override unit 480 may receive an external indication via the communication unit 460 to engage in an override mode for a predetermined period of time.

In an embodiment, components of IMD 400 (i.e. controller 410, signal generation unit 420, etc.) are all coupled to support member 401 as described in detail above. Furthermore, support member 401 and components of IMD 400 may be completely integrated into a compact and unitary device. That is, each component of IMD 400 may be integral to the support member 401. Thus, in such embodiments, the IMD 400 may be a complete standalone device without the need for any external devices to be carried around by a patient. As such, one of the many advantages of the IMD is that it may allow a patient to be completely ambulatory when the IMD is implanted, and providing maximum quality of life to the patient.

It is also contemplated that various embodiments of the IMD may be temporary or permanent. That is, in some embodiments, IMD may be constructed to be inexpensive and easily disposable. For example, in particular embodiments, the IMD may be designed to be replaced once the power supply has been consumed. Such devices may be resident in the body of the patient for from several months up to several years, although shorter or longer residence times are possible. In other embodiments, IMD may be designed for permanent or long term operation such it will not need replacement for time periods of 10 years or more. Another advantage of the device is that it is easily removable.

Figure 7:
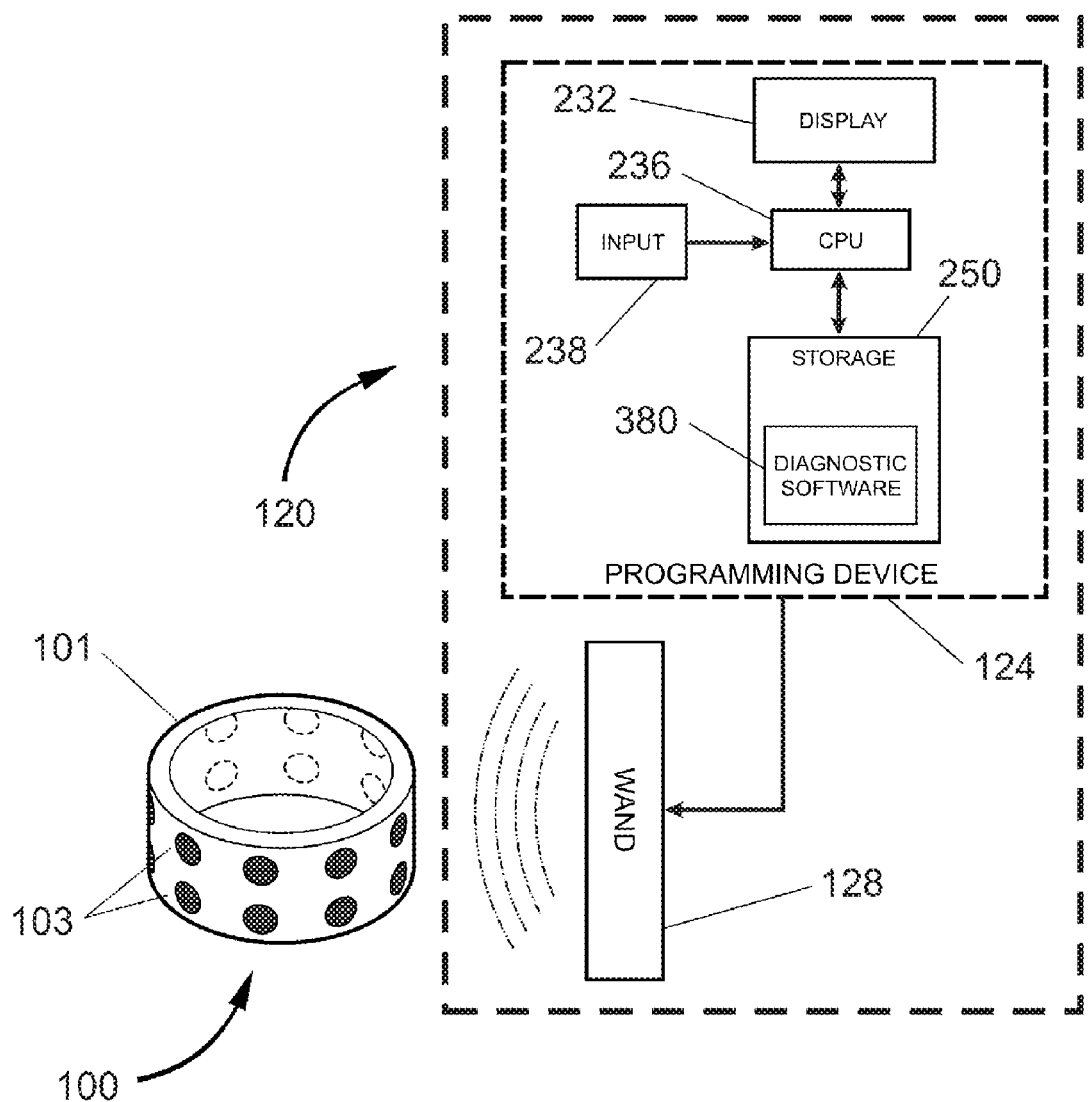
FIG. 7 is a block diagram illustrating an external programming system and wand for communication and programming of implantable medical devices according to the present invention.

FIGS. 2 and 7 illustrate an external unit or programming system 120 comprising a programming device 124 coupled to a wand 128 for transmitting and receiving signals to and from the IMD 100. As mentioned above with respect to FIG. 4, the IMD 100 preferably comprises a signal or pulse generator 122, and a controller to control the generation and delivery of the electrical signal by the pulse generator 122. The controller preferably is, or includes a central processing unit (CPU) such as a low-power, mixed-signal microcontroller. In alternative embodiments, the controller and pulse generator 122 may be part of an external programming system 120, described in more detail below.

In an additional embodiment, the IMD 100 comprises a power supply which is coupled to the support member 101, and to the pulse generator 102. The power supply is typically a battery, such as a lithium carbon monofluoride (LiCFx), lithium ion, nickel cadmium alkaline, and the like. In a preferred embodiment, the power supply comprises a battery located inside support member 101 and coupled to the pulse generator 102. In an alternative embodiment, the power supply is rechargeable. In one aspect, the power supply may be wirelessly rechargeable. A wirelessly rechargeable power supply may include an external power supply on the outside of the patient's body, inductively coupled to an implanted rectifier and/or capacitor attached to the support member 101. Such a power supply may be charged from outside the patient's body without requiring removal of the medical device. In another embodiment, an external power supply may be part of an external programming system 120 as will be described below.

FIGS. 2 and 7 further illustrate a programming system 120 comprising a programming device 124 coupled to a wand 128, for transmitting and receiving wireless signals (e.g., RF signals) to and from the IMD 100. The programming device 124 may comprise a personal computer, personal digital assistant (PDA) device, or other suitable computing device consistent with the description contained herein. Methods and apparatus for communication between an IMD 100 and an external programming system 120 are known in the art. In one embodiment, the IMD 100 includes a transceiver (such as a coil) that permits signals to be communicated wirelessly and non-invasively between the programming device 124 (via the external wand 128) and the implanted IMD 100. Wand 128 facilitates wireless communication and may be placed on the skin of the patient's body overlying the implant site of the IMD 100. The programming system 120 may also monitor the performance of the IMD 100 and download new programming parameters to define the therapeutic electrical signal (e.g., on-time, off-time, pulse width, current amplitude, frequency) into the IMD 100 to alter its operation as desired. In various embodiments, portions of the programming system may be integrated into the IMD 100, itself, or may be external to the IMD 100.

FIG. 7 shows a block diagram of one embodiment of the programming system 120. As shown, the programming system 120 is external to the patient's body, and includes the programming device 124 and the wand 128. Programming system 120 generally assists, controls, and/or programs the IMD 100 and may also receive data from the IMD referring to status and operational conditions stored in or generated by the IMD, such as battery and lead diagnostic information, remaining battery life calculations, current programming parameters, patient identification information, programming history information, etc. Thus, in an embodiment, the IMD 100 generates a therapeutic pulsed electrical signal for application to the vagus nerve 133 in a patient under the control of programming system 120.

Programming device 124 preferably includes a central processing unit (CPU) 236 such as a low-power, mixed-signal microcontroller. In general, any suitable processor can be used to implement the functionality performed by the programming device 124 as explained herein. It will be appreciated that some features of the programming system 120 may also be provided in whole, or in part, by the IMD 100, and vice versa. Thus, while certain features of the present invention may be described as part of the IMD 100, it is not intended thereby to preclude embodiments in which the features are provided by the programming system 120. Likewise, describing certain features herein as part of the programming system 120 does not preclude embodiments in which the features are included as part of the IMD 100.

The CPU 236 of programming device 124 is preferably coupled to a memory 250. The memory 250 may comprise volatile (e.g., random access memory) and/or non-volatile memory (e.g., read only memory (ROM), electrically-erasable programmable ROM (EEPROM), Flash memory, etc.). Memory 250 may comprise any suitable storage medium. Examples of suitable storage media include without limitation, USB flash drives, Compact Flash cards, memory sticks, Smart Media cards, Secure Digital (SD) cards, xD cards, CD-ROM, DVD-ROM, tape drives, Zip disks, floppy disk, RAM, hard drives, etc. The memory 250 may be used to store code (e.g., diagnostic software) that is executed by the CPU 236. The executable code may be executed directly from the non-volatile memory or copied to a volatile memory for execution therefrom.

In addition, programming device 124 of programming system 120 may have a display or output 232 such that a user may monitor the functions or properties of the IMD 100. In some embodiments, programming system 120 may have a graphical user interface. In preferred embodiments, a user may input parameter settings using an input device 238 through the graphical user interface on the display 232, or other input means. Memory 250 may store data received from the IMD 100 or may be used to store software 380 (e.g., diagnostic software, therapy programs, code, etc.) that is executed by the CPU 236. The executable code may be executed directly from the non-volatile memory or copied to the volatile memory for execution therefrom.

In one embodiment, the programming system 120 may be used by a physician as part of an office computer system, in which the IMD 100 is queried regularly during office visits by the patient. According to another embodiment, programming system 120 may be ambulatory, and wand 128 may be continuously in contact with the patient's skin near implant site (i.e., the abdominal region) to provide continuous control of IMD 100 in conjunction with a portable handheld device 124 that may comprise, e.g., a PDA. Wand 128 is coupled to the programming device 124 which may be conveniently worn by the patient on a belt, pocket, and the like. In another embodiment, programming device 124 and wand 128 are integrated into a single device which is kept in continuous proximity to the IMD 100 so as to maintain wireless communication with the IMD 100 through the skin.

Figure 8:
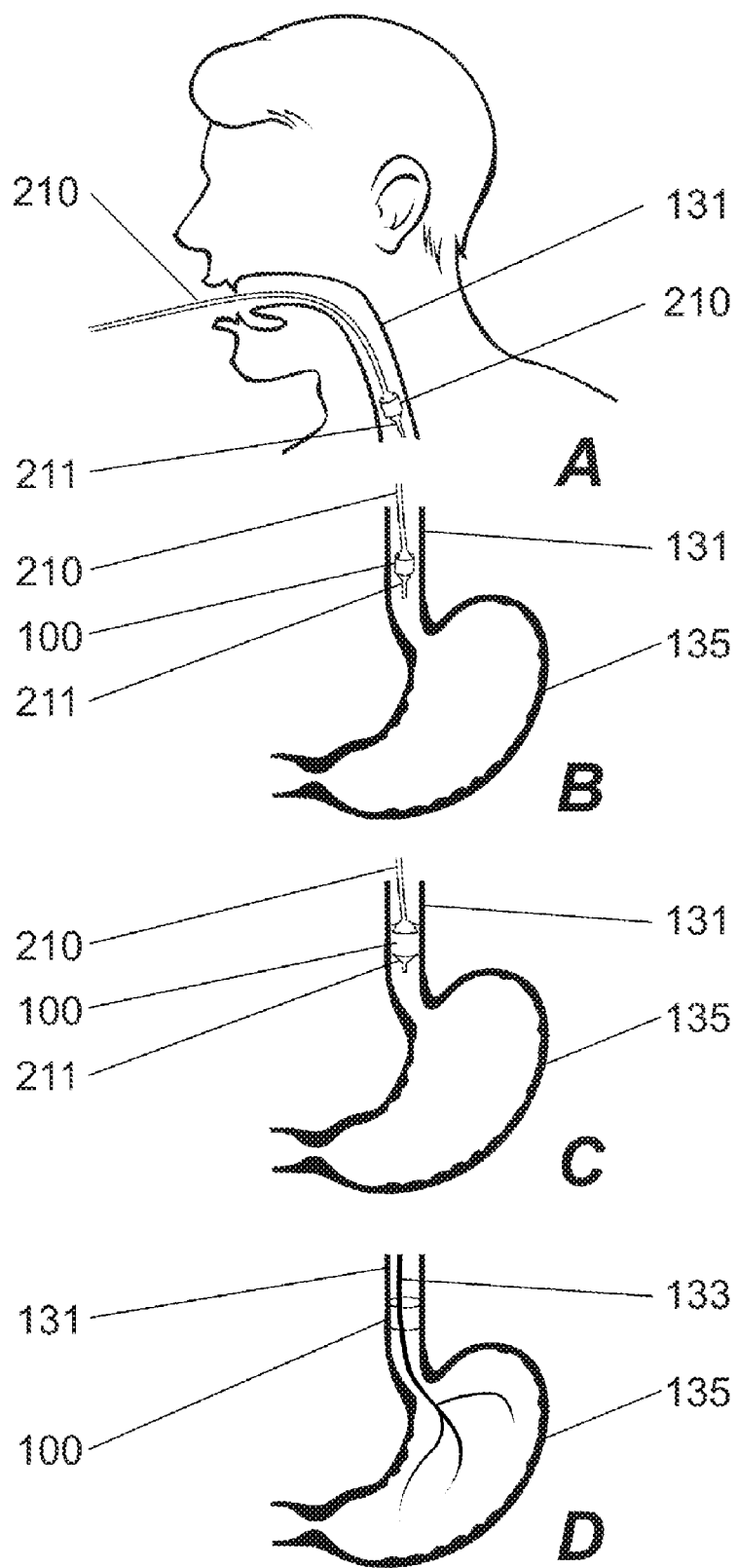
FIGS. 8A-D illustrate an embodiment of a method of non-surgically implanting an IMD for providing trans-esophageal VNS to a patient to treat a medical condition.

In an embodiment of a method of providing an electrical signal to a vagus nerve, an IMD 100, as described in detail above, is implanted in the esophagus 131 of a patient. See FIGS. 8A-D. In at least one embodiment, the IMD 100 is implanted in the lower or abdominal portion of the esophagus 131 at or below the patient's diaphragm, e.g., where the anterior and posterior vagus nerves are attached to the exterior wall of the esophagus 131 near the esophagogastric junction. Preferably, the IMD 100 is delivered to the implantation site in the esophagus 131 orally i.e. through the mouth and esophagus as shown in FIGS. 8A and 8B. In a particular embodiment, IMD 100 may be implanted via a catheter delivery system. Specifically, IMD 100 may be mounted at the end of a catheter 210, e.g., at a balloon portion 211 of a balloon catheter in its contracted position. The catheter 210 and IMD 100 may then be inserted into the patient's mouth and throat (i.e. orally), and advanced into the esophagus as shown in FIG. 8A. Preferably, the catheter 210 is inserted until the distal tip is near the esophagogastric junction (i.e., at the intersection of the esophagus and the stomach) as this portion of the esophagus 131 is where the vagus nerve 133 reforms from the esophageal plexus to form the anterior and posterior vagal trunks. See FIG. 8B.

Once the distal tip of catheter 210 is disposed at the desired implantation site for IMD 100, the IMD 100 is deployed (for example, to an expanded position) and anchored to the inner wall of the esophagus. If a balloon catheter is used, the balloon portion may be inflated to expand the support member 101. A balloon catheter may be used, for example, in conjunction with a support member comprising a stent or stent-like retainment element. Alternatively, the support member 101 may comprise a wire or band of a shape-memory metal such as Nitinol or a resilient polymer to provide strength and additional support to the support member 101. The support member 101 (with the retainment element) may be wrapped around, folded, compressed or otherwise reduced to a contracted position and retained in position on the catheter by sutures, releasable wires, or other constraining means known in the art, where a constraint is needed.

Once in position, FIG. 8C, the IMD 100 deployed into place against the inner wall of the esophagus, FIG. 8D by, for example, removing a the constraining means or expanding a balloon catheter. The IMD 100 may then be anchored in place using anchors known in the art, e.g., sutures, barbs, staples, adhesives, pins, etc. In one embodiment, the anchors are the electrodes, which comprise barbs to engage and penetrate into the wall of the esophagus. In another embodiment, anchors are not used, and the device may be retained in place solely by a retainment element, such as a C-shaped spring embedded in the support member 101.

In one embodiment, IMD 100 is implanted such that electrodes 103 are in contact with the inner wall surface of the esophagus 131. Once implanted, the IMD 100 provides electrical signal therapy (e.g., vagus nerve stimulation) to a vagus nerve by applying a therapeutic electrical signal through one or more electrodes 103 to the inner surface of the esophagus wall, through the wall of the esophagus, and to the vagus nerve 133 on the outer surface of the esophagus 131. In another embodiment, at least one electrode penetrates into the wall of the esophagus, and the electrical signal is applied to the wall of the esophagus, penetrates the outer wall, and generates action potentials in the vagus nerve. The electrical signal may be defined an a variety of ways known in the art using a number of different parameters of the signal such as without limitation, pulse width, current amplitude, frequency, on-off time, duty cycle, number of pulses per burst, interburst period, interpulse interval, burst duration, or combinations thereof. In general, these parameters may be adjusted through the programming system 120.

Vagus nerve stimulation (VNS) may involve non-feedback stimulation characterized by a number of parameters. Specifically, vagus nerve stimulation may involve a series of electrical pulses in bursts defined by an "on-time" and an "off-time." During the on-time, electrical pulses of a defined electrical current (e.g., 0.5-10.0 milliamps) and pulse width (e.g., 0.25-1.5 milliseconds) are delivered at a defined frequency (e.g., 20-30 Hz) for the on-time duration, usually a specific number of seconds, e.g., 7-120 seconds. The pulse bursts are separated from one another by the off-time, (e.g., 30 seconds-5 minutes) in which no electrical signal is applied to the nerve. The on-time and off-time parameters together define a duty cycle, which is the ratio of the on-time to the combination of the on-time and off-time, and which describes the percentage of time that the electrical signal is applied to the nerve. In other embodiments, vagus nerve stimulation may comprise a feedback stimulation scheme.

In VNS, the on-time and off-time may be programmed to define an intermittent pattern in which a repeating series of electrical pulse bursts are generated and applied to the vagus nerve. Each sequence of pulses during an on-time may be referred to as a "pulse burst." The burst is followed by the off-time period in which no signals are applied to the nerve. The off-time is provided to allow the nerve to recover from the stimulation of the pulse burst, and to conserve power. If the off-time is set at zero, the electrical signal in conventional VNS may provide continuous stimulation to the vagus nerve. Typically, however, the ratio of "off-time" to "on-time" may range from about 0.5 to about 10.

In addition to the on-time and off-time, the other parameters defining the electrical signal in conventional VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-150 Hz (i.e., 20 pulses per second to 150 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Accordingly, the electrical signal may be varied in a number of ways known in the art using a number of different parameters of the signal such as without limitation, pulse width, current amplitude, frequency, on-off time, duty cycle, number of pulses per burst, interburst period, interpulse interval, burst duration, or combinations thereof. In general, these parameters may be adjusted through the programming system 120.

It is envisioned that the disclosed device and methods may have many applications associated with vagus nerve stimulation or VNS therapy. Embodiments of the IMD may be used to treat a wide variety of medical conditions without exposing the patient to surgical complications, including without limitation epilepsy, neuropsychiatric disorders (including but not limited to depression), eating disorders/obesity, traumatic brain injury/coma, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, and reproductive endocrine disorders (including fertility) in a patient. The IMD may be easily deployed and may also avoid undesired side effects, in particular voice alteration, by providing a therapeutic electrical signal to the vagus nerve in a location remote from the larynx compared to conventional vagus nerve stimulation systems implanted in the neck area.

While embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

In an alternative embodiment of the present invention, electrical signal may be applied from the inner lumen of the esophagus using implantable medical devices coupled directly to the inner lumen of the esophagus. A signal applied from the inner lumen of the esophagus may be utilized to target a vagus nerve. Due to the proximity of portions of the vagus nerve and connections of portions of the vagus nerve to the esophagus, a stimulation signal delivered from the esophagus, i.e., the inner lumen of the esophagus, and through the wall thereof, may provide for effective electrical signal therapy for treating depression, epilepsy, obesity and/or various medical conditions.

The celiac ganglia of the vagus nerve is proximate to the outer wall of the abdominal esophagus. The celiac ganglia also connects to the greater splanchnic and the lesser splanchnic nerves. The function of the esophagus is to convey food from the pharynx to the stomach. The esophagus is generally defined as the region proximate to the pharynx in the back of the oral cavity, extending downwards proximate to the trachea to the thoracic cavity, into the diaphragm, and connecting to the stomach in the abdominal cavity. An electrical signal applied to the inner lumen of the esophagus in the abdominal region may provide for substantially effective stimulation of the vagus nerve at a location prior to substantial branching of the vagus nerve.

Figure 9:
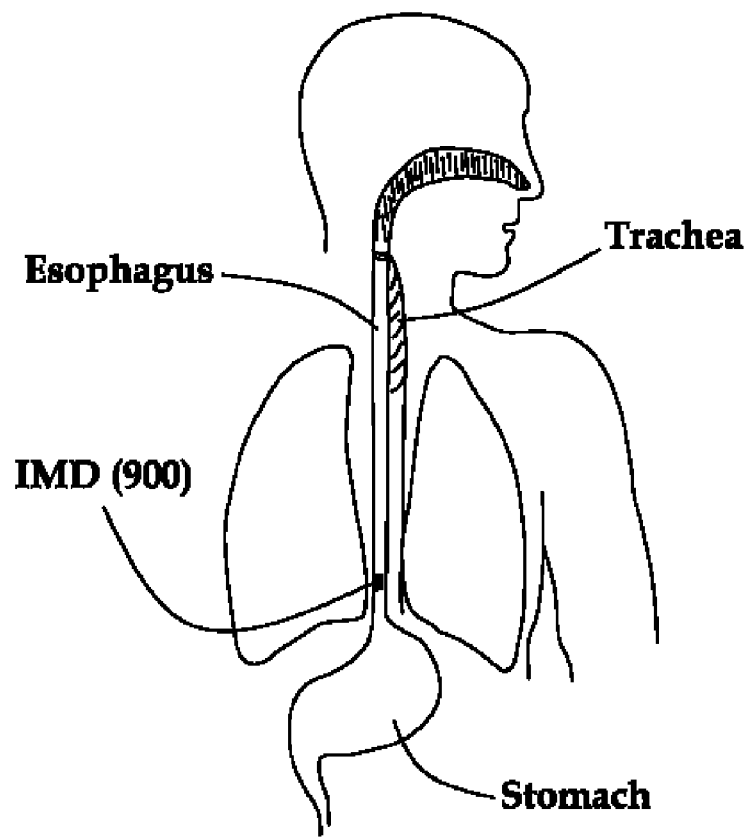
FIG. 9 depicts a stylized depiction of an esophagus in which an esophageal implantable medical device is implanted in the abdominal region, in accordance with one illustrative embodiment of the present invention.

FIG. 9 depicts a stylized depiction of an esophagus in which an esophageal implantable medical device (IMD) 900 is implanted in the abdominal region, in accordance with one illustrative embodiment of the present invention. In one embodiment, the IMD 900 illustrated in FIG. 9 may comprise substantially similar components as illustrated in the implantable medical device 400 of FIG. 4. Therefore, in one embodiment, the block diagram of FIG. 4 represents the components of the IMD 900.

Various factors may have to be considered when implanting the IMD 900 within the inner lumen of the esophagus. The esophagus transports food to the stomach by coordinated contractions in its muscular lining. This process is performed in an automatic fashion. Further, similar to other parts of the digestive tube, the esophagus contains four tunics. However, the tunics relating to the esophagus are different as compared to other portions of the digestive system. The muscular tunic in the esophagus contains a variable amount of striated muscle. This is in contrast to the smooth muscle found in the stomach and intestine. Further, the esophagus is embedded in connective tissue; its outer tunic is referred to as the adventitia.

In some cases, the IMD 900 should be sufficiently resilient to withstand a relatively harsh bio-environment. The esophagus is generally exposed to rough and abrasive food materials, including fragments of bones, fibrous plant leaves, etc. The esophagus is lined with stratified squamous epithelium to enhance resistance to trauma. The muscular layers of the esophagus are normally pinched together at both upper and lower ends by the sphincters. A swallowing motion causes the sphincters to relax automatically to allow food and drink to pass from the mouth to the stomach. The muscle is then closed rapidly to prevent swallowed food from leaking out of the stomach back into the esophagus. Therefore, the inner lumen of the abdominal esophagus experiences an appreciable amount of movement. The movement of the inner lumen of the abdominal esophagus, as well as exposure to the food material traveling through the esophagus, prompts bio-environmental considerations when implanting an IMD 900 into the lumen of the esophagus.

The esophagus generally experiences a peristaltic movement, which is a rhythmic contraction of muscles to propel contents through the digestive tract. The esophagus experiences at least two types of peristaltic movement. The esophagus experiences a primary peristaltic wave during swallowing. The primary peristaltic wave forces the food down the esophagus into the stomach in a wave lasting a few seconds, e.g., 8-9 seconds. The wave travels down to the stomach even if the food descends at a greater rate than the wave itself. The esophagus may also experience a secondary peristaltic wave when the food travels down the esophagus at a slower rate than the primary peristaltic wave. Upon this occurrence, receptors in the esophageal lining are stimulated and a local reflex response is created. Due to the special movements of the esophagus, as well as exposure of material in the esophagus, particular attention may be paid to the material, shape, and the attachment features of the esophageal IMD 900.

Figure 10:
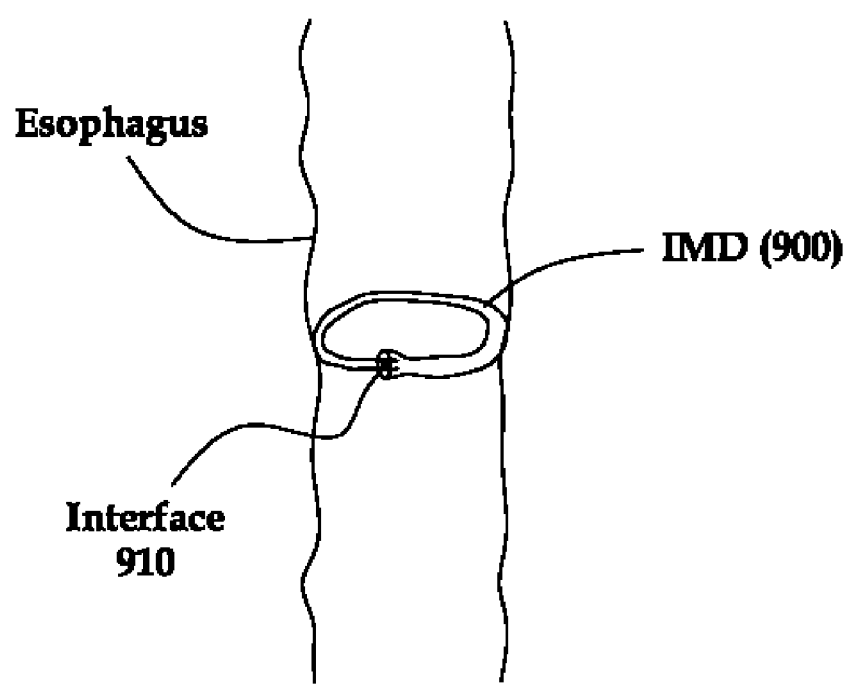
FIG. 10 depicts an esophageal IMD for placement in an abdominal region of patient esophagus, in accordance with one illustrative embodiment of the present invention.

Turning now to FIG. 10, an esophageal IMD 900, in accordance with one illustrative embodiment of the present invention, is depicted. In one embodiment, the IMD 900 illustrated in FIG. 10 is a telescopic ring-type device that comprises sub-parts that are capable of performing a repetitive telescoping action. The IMD 900 is substantially tightly placed in the esophagus. As the peristaltic movements of the esophagus take place, a telescoping action is provided for accommodating the changes in the size of the esophagus. A spring action may be provided to maintain a minimum amount of force against the wall of the esophagus during contractions of the esophagus.

Figure 11A:
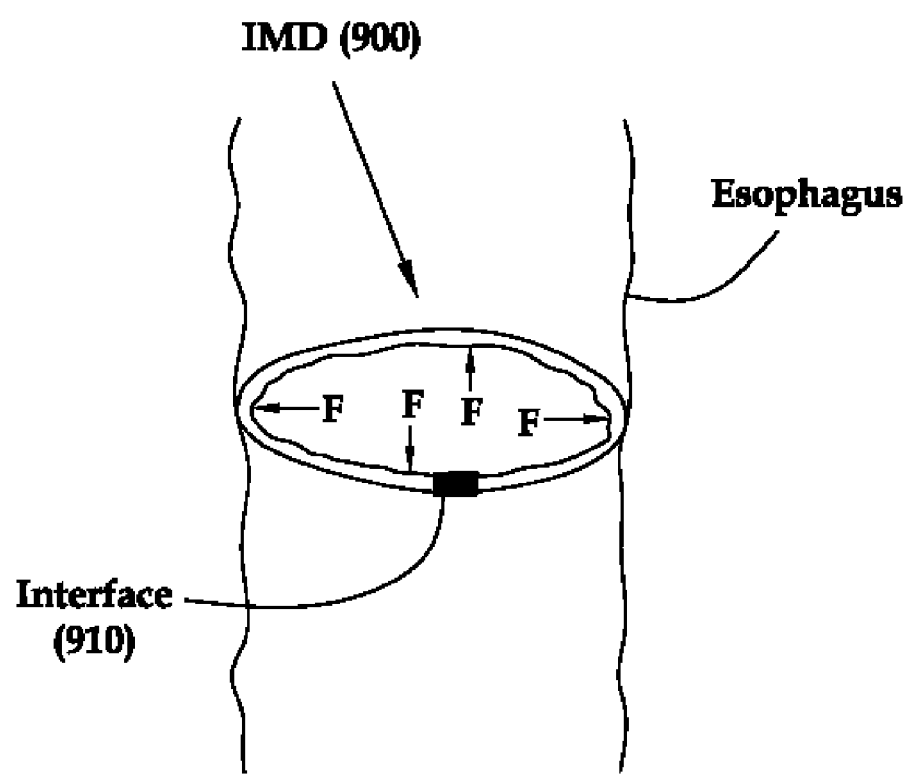
FIGS. 11A-B depict stylized illustrations of the abdominal region of the esophagus and the IMD of FIG. 9.
Figure 11B:
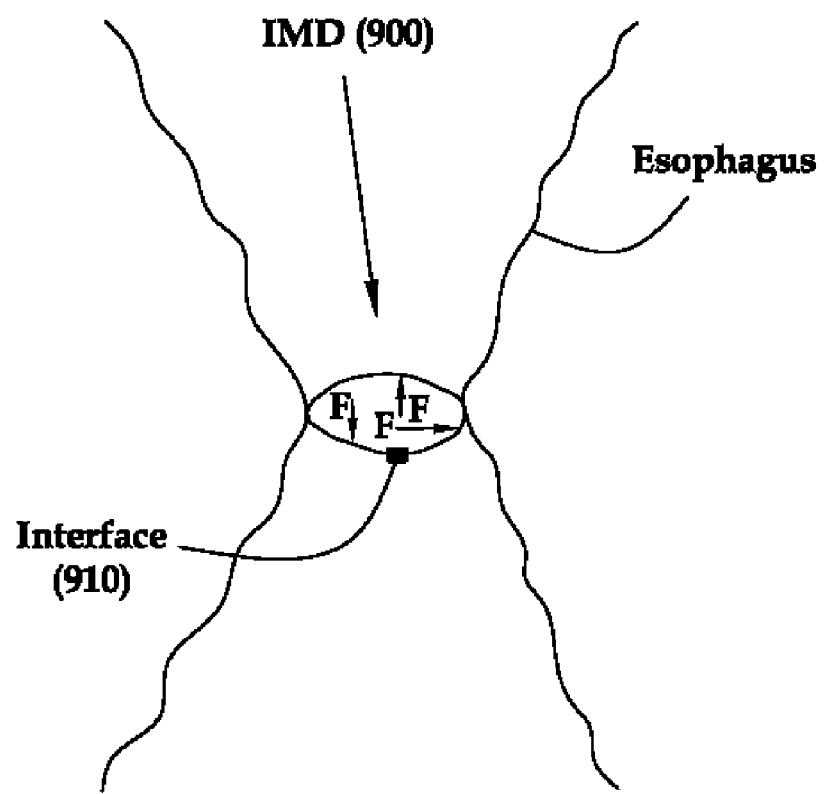

As illustrated in FIGS. 11A and 11B, which depict stylized illustrations of the esophagus and the IMD 900, the esophagus may undergo a relative change in a relative change in the cross-sectional area due to peristaltic movement. The stylized depiction of the IMD 900 positioned in the esophagus of FIG. 11A illustrates an esophagus that is in a normal state. Due to the spring-like action provided by the IMD 900, a minimum amount of force may be applied to the inner walls of the esophagus. This force may act to maintain the position of the IMD 900 in the esophagus.

Further, in one embodiment, the block diagram representation of FIG. 4 is representative of the components embodied in the IMD 900. In an alternative embodiment, the IMD 900 may comprise the power supply 430 and the signal generation unit 420 for delivering an electrical signal for stimulating a portion of a cranial nerve, such as the vagus nerve. In yet another alternative embodiment, the IMD 900 may comprise power supply 430, the signal generation unit 420, and the communication coil 460, for receiving a communication signal from the external unit 120 for delivering therapeutic electrical signal.

As illustrated in FIG. 11B, due to peristaltic movement of the esophagus, the relative cross-sectional area of the inner portion of the esophagus may become contracted and smaller. The telescoping action provides for collapsing a first member or portion of the IMD 900 into a second member or portion of the IMD 900 to accommodate the reduction in diameter of the esophagus. Between the first member and the second member is an interface 910, where the distal ends of first and second members meet during a normal state of the esophagus. As illustrated in FIG. 11B, a minimum amount of force is maintained while the circumference of the telescopic IMD 900 is reduced due to the telescopic action. In one embodiment, the spring action force described in relation to the IMD 900 is a passive spring action force.

In an alternative embodiment, a controller in the IMD 900 (similar to the controller 410 illustrated in FIG. 4) may detect peristaltic movement of the esophagus and cause an activation of a spring-like device within the IMD 900 (i.e., an active spring action force). In this manner, the controller 410 may activate the reduction of force of a spring action device within the IMD 900, thereby allowing for easier telescopic movement for reduction of the circumference of the IMD 900 to respond to the reduction in the cross-sectional area of the esophagus. The spring action device may reside in the second member. Upon detecting the end of the peristaltic movement, the telescopic ring device structure may cause the increase in force of the spring-like device to expand the circumference of the IMD 900.

Figure 12A:
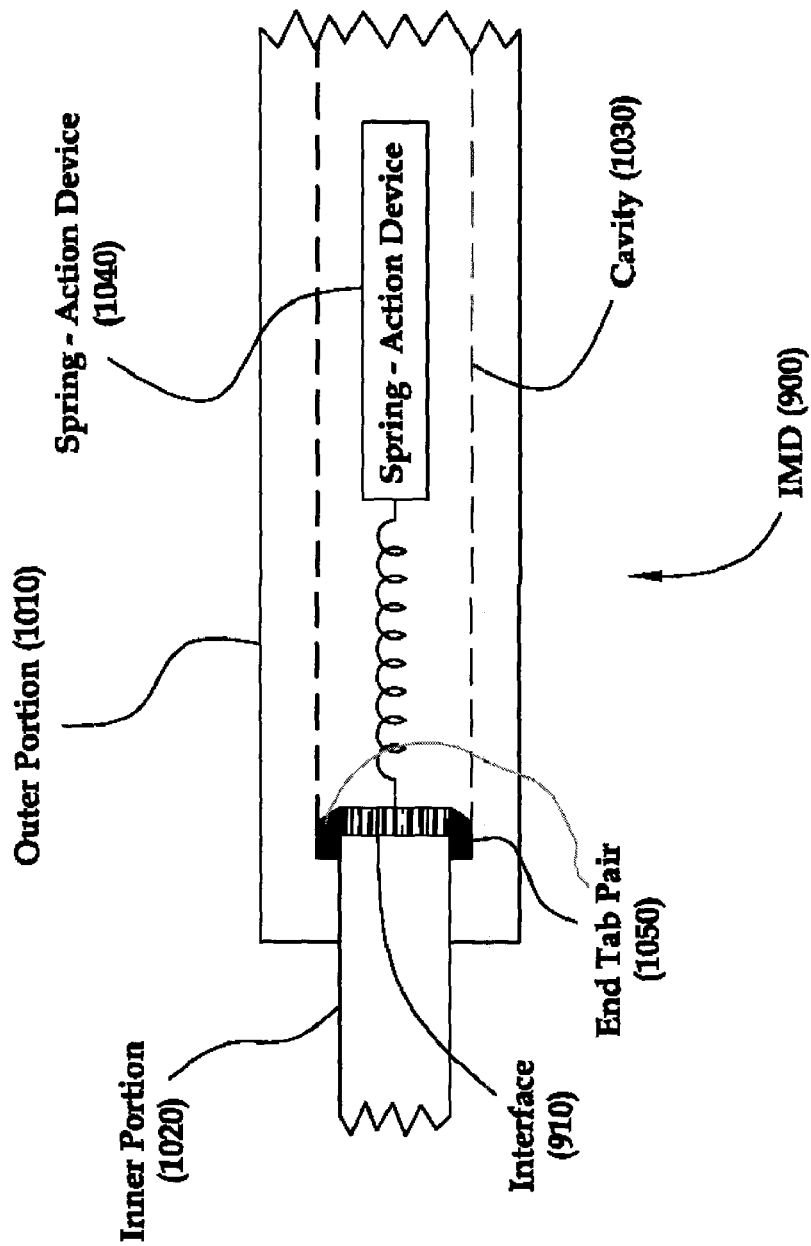
FIGS. 12A-B depict stylized cross-sectional views of a portion of a telescopic ring-type esophageal IMD in accordance with one illustrative embodiment of the present invention.

Turning now to FIG. 12A, a stylized partial cross-sectional view of a portion of the telescopic ring-type IMD 900 is depicted in accordance with one illustrative embodiment of the present invention. In one embodiment, the IMD 900 comprises an inner portion 1020 (i.e., a first member) and an outer portion 1010 (i.e., a second member). In one embodiment, the inner portion 1020 is a male portion and the outer portion 1010 is a female portion. At the intersection of the inner and outer portions 1020, 1010 is the interface 910. The inner portion 1020 is capable of moving in and out relative to the outer portion 1010. Therefore, the interface 910 moves within the outer portion 1010 based upon the force exerted by the esophagus upon the IMD 900.

In one embodiment, the outer portion 1010 comprises a cavity 1030. The cavity 1030 is positioned and of such a size that the inner portion 1020 may move within the cavity 1030. Therefore, when a peristaltic movement occurs and the contraction of the esophagus results, the cavity 1030 is capable of accommodating the inner portion as it is pushed into the cavity 1030.

The outer portion 1010 may also comprise a spring action device 1040. The representation of the spring device 1040 in FIG. 12A is provided in a stylized manner for exemplary purposes and those skilled in the art, having benefit of the present disclosure, may employ a variety of types of spring action devices and remain within the spirit and scope of the present invention. Further, the inner portion 1020 may comprise a pair of end tabs 1050 to prevent the interface 910 of the inner portion 1020 from completely disengaging from the outer portion 1010. The spring action device 1040 provides for predetermined exertion of force being applied radially outwards from the IMD 900 onto the inner wall of the esophagus.

Figure 12B:
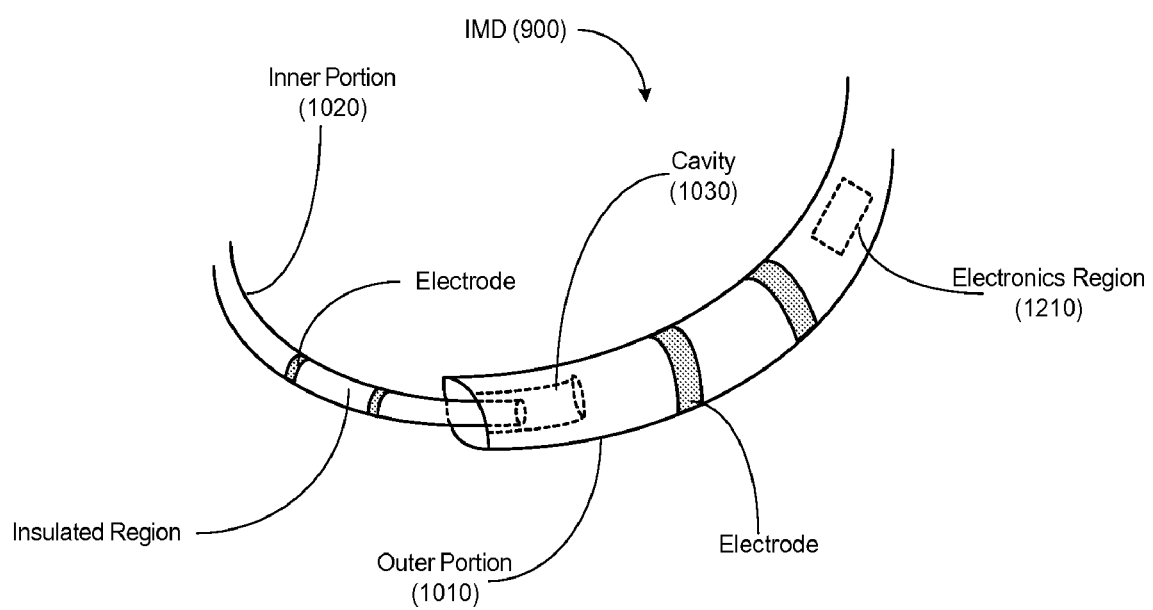

FIG. 12B illustrates a stylized representation of the inner and outer portions 1020, 1030 of the IMD 900, in accordance with one illustrative embodiment of the present invention. As illustrated in FIG. 12B, the inner portion 1020 and the outer portion 1020 may comprise a plurality of electrodes. The electrodes may be conductive regions that are strategically placed on the IMD 900 for delivering targeted therapy to the inner wall of the esophagus in order to stimulate a portion of the vagus nerve. The portion between the electrodes may be an insulated region. In one embodiment, the insulated region and electrodes may be substantially flush relative to each other as to allow for movement within the inner wall of the esophagus while allowing for patient comfort during telescopic movements of the IMD 900. FIG. 12B also illustrates an electronics region 1210 within the IMD 900 that may include various components substantially similar to the components illustrated in the IMD 400 of FIG. 4.

Figure 13:
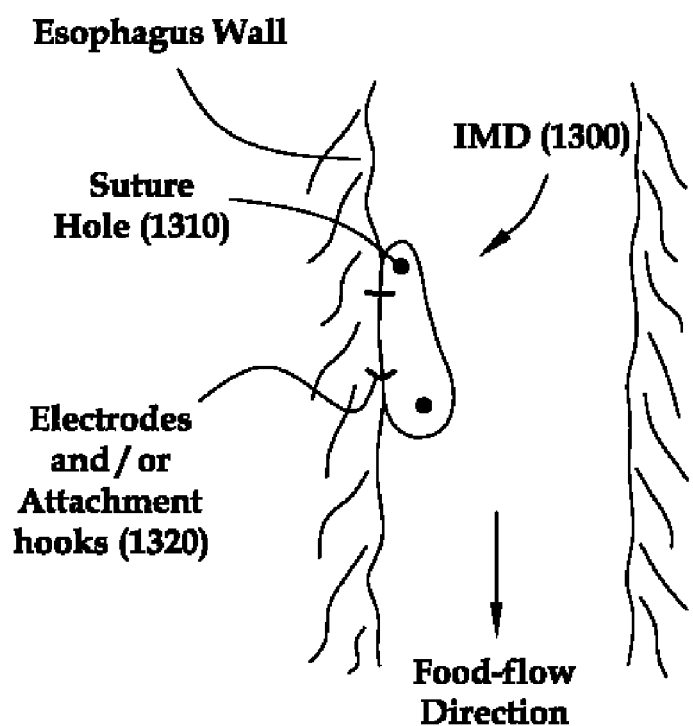
FIG. 13-17 are stylized depictions of an implantable device implanted into an inner portion the abdominal region of the esophagus in accordance with yet another illustrative embodiment of the present invention.

Turning now to FIGS. 13-17, stylized depictions of an IMD implanted into the esophagus in accordance with yet another illustrative embodiment of the present invention are provided. FIG. 13 illustrates a low profile shaped IMD 1300. The IMD 1300, in one embodiment, may be provided in an elongated, narrow body e.g., shaped similar to a leech. The outer shell of the IMD 1300 comprises a first surface that is substantially minimally obstructive in nature. The second surface may be shaped such that it conforms to at least a portion of the inner wall of the esophagus. The low profile shape of the first surface provides for withstanding the flow of food and liquid. The abrasive and rough food material traveling through the esophagus may flow more efficiently through the esophagus, relatively unimpeded by the presence of the IMD 1300.

The IMD 1300 may comprise one or more suture structures (e.g., holes, loops, etc.) 1310, which may be used to suture the IMD 1300 to a portion of the inner wall of the esophagus. Known suture techniques may be used to suture the IMD 1300 to the inner wall of the esophagus. Further, the IMD 1300 may comprise one or more attachment hooks 1320. The attachment hooks 1320 may be formed of conductive material and may protrude from the IMD 1300. The attachment hooks 1320 may be used as hooks to penetrate the inner wall of the esophagus to stabilize the position of the implanted IMD 1300. In one embodiment, the attachment hooks 1320 may also function as the electrodes that carry stimulation signals from the IMD 1300 in the inner lumen of the esophagus across the esophagus wall for providing electrical signal to the vagus nerve.

Figure 14:
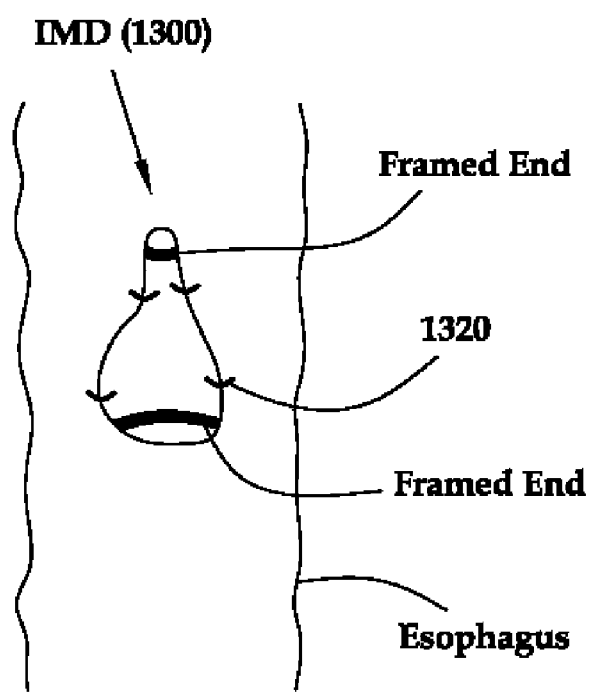

As illustrated in FIG. 14, the IMD 1300 may comprise a first formed end and a second formed end. The formed ends may provide for a relatively sleek shape of the IMD 1300. This feature may provide for decreasing the likelihood of obstruction of the flow of food material traveling down the patient's esophagus. In an alternative embodiment, the framed ends may comprise one or more suture structures (e.g., suture hole(s), suture loop(s), etc) and/or other attachment mechanisms to secure the IMD 1300 to the inner lumen of the abdominal esophagus.

Figure 15:
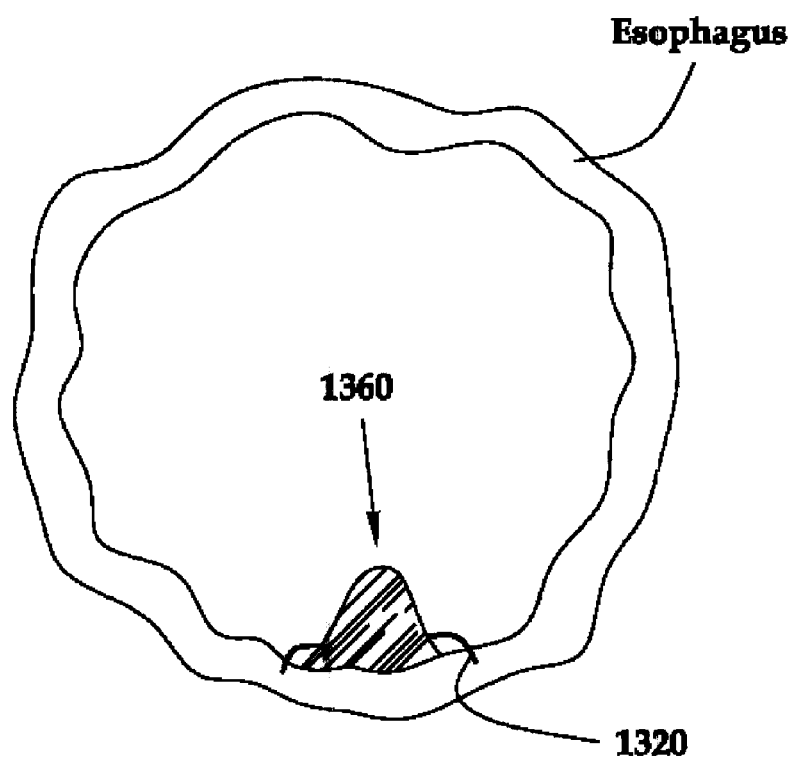

Turning now to FIG. 15, a stylized cross-sectional, top view of the esophagus, in accordance with one illustrative embodiment of the present invention, is depicted. The IMD 1300 is shown attached to an inner wall of the esophagus and affixed using hooks 1320. The hooks 1320, as described above, may function as electrodes. As illustrated in FIG. 15, the IMD 1300 is positioned in the inner wall of the esophagus as to minimize intrusion against the flow of food and fluids.

Figure 16:
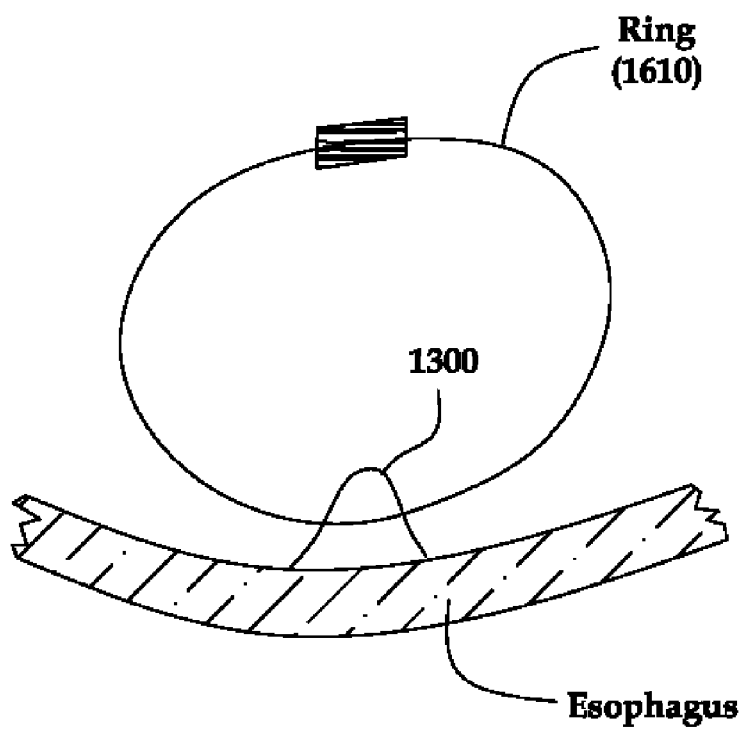
Figure 17:
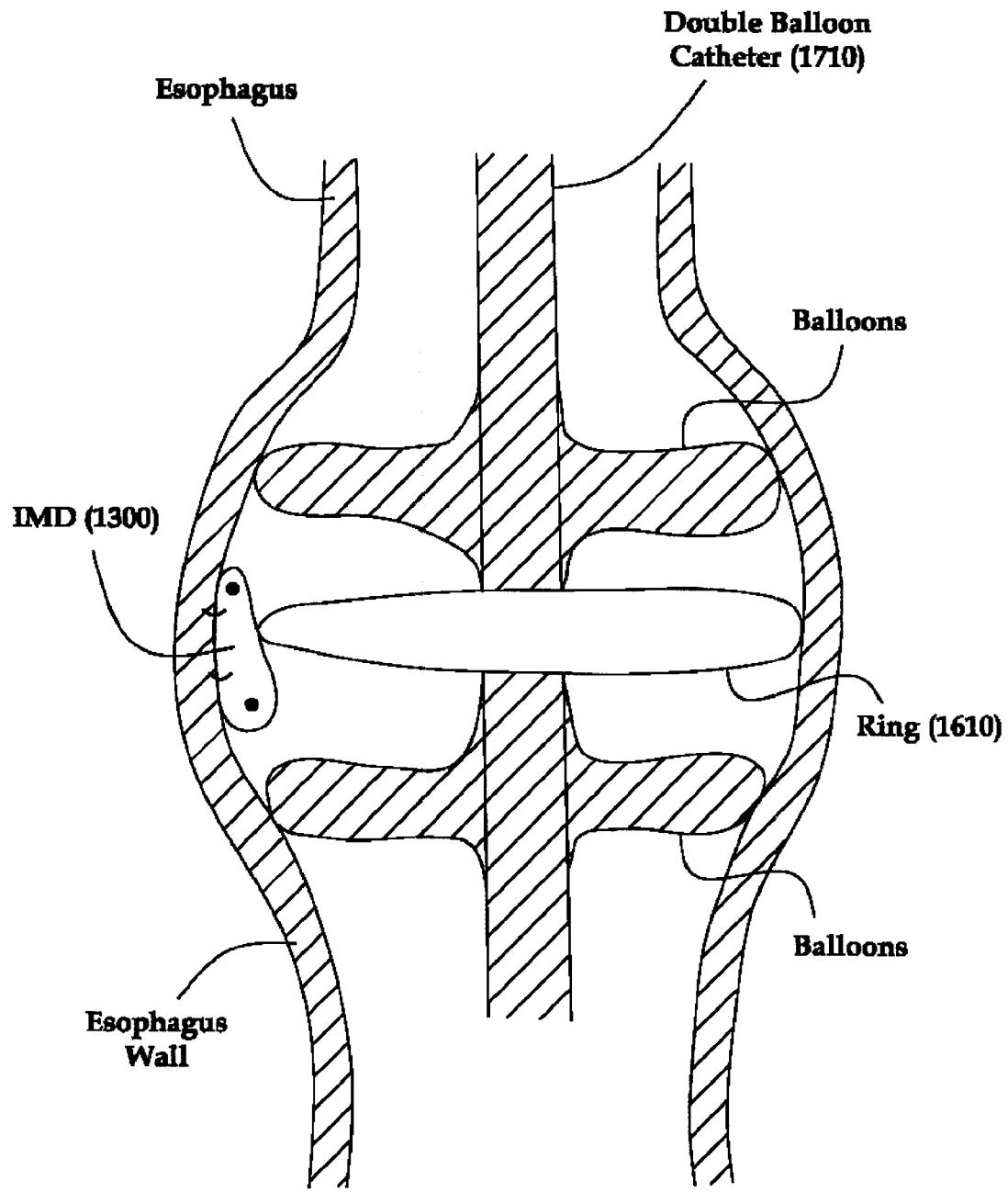

Turning now to FIG. 16, a ring 1610, is shown attached to the IMD 1300, which is coupled to the inner lumen of the esophagus. In one embodiment, the ring may be used to position and install the IMD 1300 in the lumen of the esophagus. Referring simultaneously to FIGS. 16 and 17, a double balloon catheter 1710 utilized for installing the IMD 1300 is illustrated. The catheter 1710 may comprise multiple balloons (e.g., first and second balloons), which may be used in conjunction with the ring 1610 to position the IMD 1300 into the inner wall of the esophagus. In one embodiment, the balloon catheter 1710 may be used to isolate one or more areas of the inner lumen of the esophagus for deploying the IMD in a body lumen for performing an operation of the target area, such as implanting an esophageal IMD. The balloon catheter 1710 may be used to temporarily expand one or more areas of the inner lumen of the esophagus to aid in the placement of the IMD 1300 into a desired area of the inner lumen of the esophagus. The ring 1610 attached to the IMD 1300 may be lowered to a desired position in the esophagus using the double balloon catheter 1710. The balloons associated with the catheter 1710 may be expanded to allow for positioning of the ring 1610 and the IMD 1300. Once the ring 1610 and the IMD 1300 are positioned in a desired location in the abdominal esophagus, the balloons of the double balloons catheter 1710 may be deflated and the catheter 1710 is extracted. In one embodiment, the ring 1610 is removed and the IMD 1300 is then left in position in the esophagus wall.

The IMD 1300 may be secured to the inner lumen of the esophagus using the hooks 1320. In an alternative embodiment, the suture structures 1310 may be used (with or without hooks 1320) to secure the IMD 1300 onto the inner lumen. In yet another alternative embodiment the ring 1610 may be left within the esophagus to ensure stability of the position of the IMD 1300. In this embodiment, the ring 1610 may be capable of telescoping movements (as previously described) to allow for proper securing of the IMD 1300 during the peristaltic movements of the esophagus. Those skilled in the art, upon a reading of the present disclosure, would readily understand that a variety of techniques may be used to secure the IMD 1300 to the inner lumen esophagus and remain within the spirit and scope of the present invention.

Further, the IMD 1300 may also comprise one or more components similar to the components of the IMD 400 illustrated in FIG. 4. In one embodiment, the block diagram of the IMD 400 in FIG. 4 also represents the block diagram of the IMD 1300. In an alternative embodiment, the IMD 1300 may comprise the power supply 430 and the signal generation unit 420 for delivering an electrical signal trans-esophageally to the vagus nerve. In embodiment, the terms "trans-esophageal" electrical signal and/or "trans-esophageally" generating electrical signal refer to electrical signals generated inside a portion of the lumen of a patient's esophagus and transmitted through the wall of the esophagus. In this embodiment, the IMD 1300 may be a simple device capable of delivering pre-programmed stimulation signals trans-esophageally from inner lumen and ultimately to a vagus nerve. In yet another alternative embodiment, the IMD 1300 may comprise power supply 430, the signal generation unit 420, and the communication coil 460 for receiving a programming signal from the external unit 120 for delivering stimulation therapy. The communication coil 460 may represent a variety of communication devices and may be collectively referred to as a communication unit.

Figure 18A:
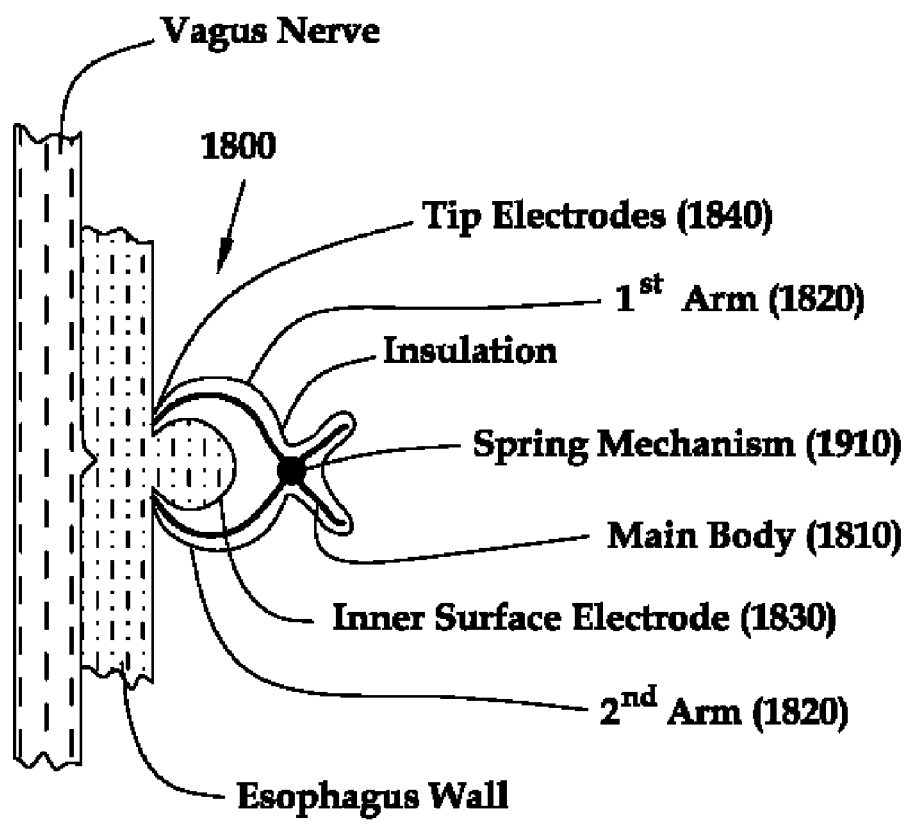
FIGS. 18A-B are stylized depictions of an implantable medical device that comprises a plurality of electrodes formed in clamp-type structures, in accordance with illustrative embodiments of the present invention.
Figure 18B:
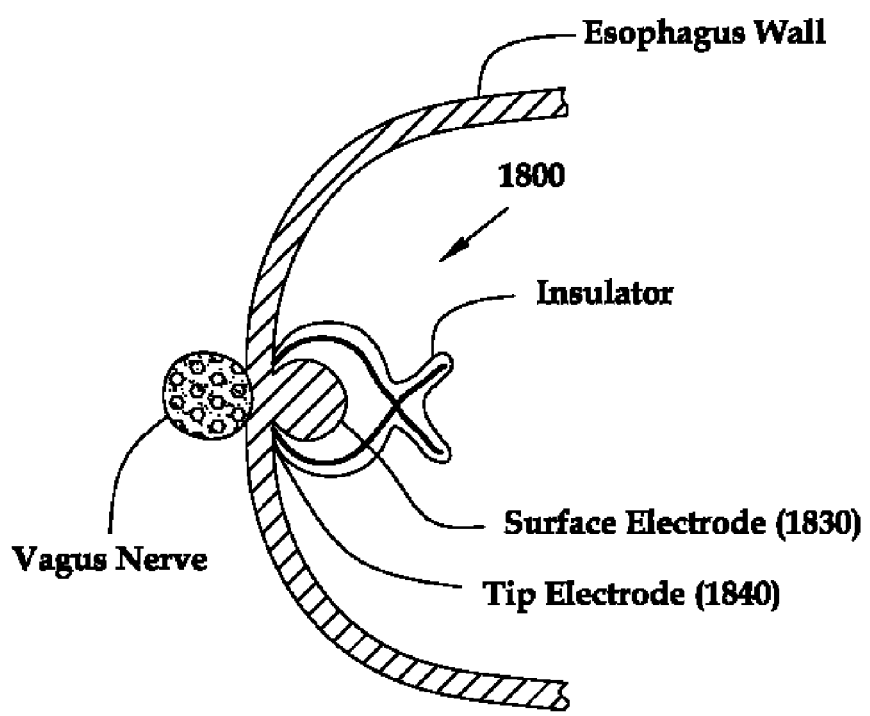

The IMDs illustrated in embodiments of the present invention may be capable of providing a control, therapeutic electrical signal defined by one or more parameters for performing stimulation of the vagus nerve. These parameters include, but are not limited to, a current amplitude, a voltage amplitude, a rate of change of said current amplitude, a rate of change of said voltage amplitude, a time period of a rate of change of said current amplitude, a time period of a rate of change of said voltage amplitude, a pulse width, a rate of change of the pulse width, a time period of a rate of change of the pulse width, a frequency, a rate of change of the frequency, a time period of a rate of change of the frequency, a signal on-time, a signal off-time, and/or a duty cycle Turning now to FIGS. 18A and 18B, stylized depictions of an implantable medical device that comprises a plurality of electrodes formed in clamp-like structures, in accordance with one illustrative embodiment of the present invention, is provided. FIG. 18A illustrates a stylized cross-sectional side view of a patient's esophagus and an IMD 1800. FIG. 18B illustrates a stylized cross-sectional top view of the patient's esophagus and the IMD 1800. The IMD 1800 is capable of providing electrical signals trans-esophageally from an inner lumen of esophagus to the vagus nerve. The IMD 1800 comprises a main body 1810, a plurality of arms 1820, a spring mechanism 1910, one or more tip electrodes 1840 coupled to the arms 1820, and at least one inner surface electrode 1830. The IMD 1800 is capable of being clamped onto the inner wall of the esophagus. When the IMD 1800 is clamped on a portion of the inner wall of the esophagus, the tip electrodes 1840 as well as the inner surface electrodes 1830, as shown in FIGS. 18A and 18B, make contact with the region of the inner lumen/portion of the esophagus proximate to the position where the IMD 1800 is secured. When the IMD 1800 is clamped in the abdominal esophagus, the tip electrodes 1840 and the surface electrode 1830 are capable of delivering a therapeutic electrical signal from an inner lumen of the esophagus to a portion of the vagus nerve outside the esophagus.

In an alternative embodiment, the clamping feature illustrated in FIGS. 18A-B may include penetrating the tip electrodes 1840 into the wall of the esophagus to facilitate trans-esophageal delivery of a therapeutic electrical signal from an inner lumen of the esophagus to a portion of the vagus nerve outside the esophagus. Portions of the IMD 1800, e.g., the spring mechanism 1910, the arms 1820, main body 1810, etc, may be covered with an insulating material to substantially prevent electrical contact between the IMD 1800 (excluding the tip electrodes 1840 and the surface electrodes 1830) and portions of the patient's esophagus.

Figure 19:
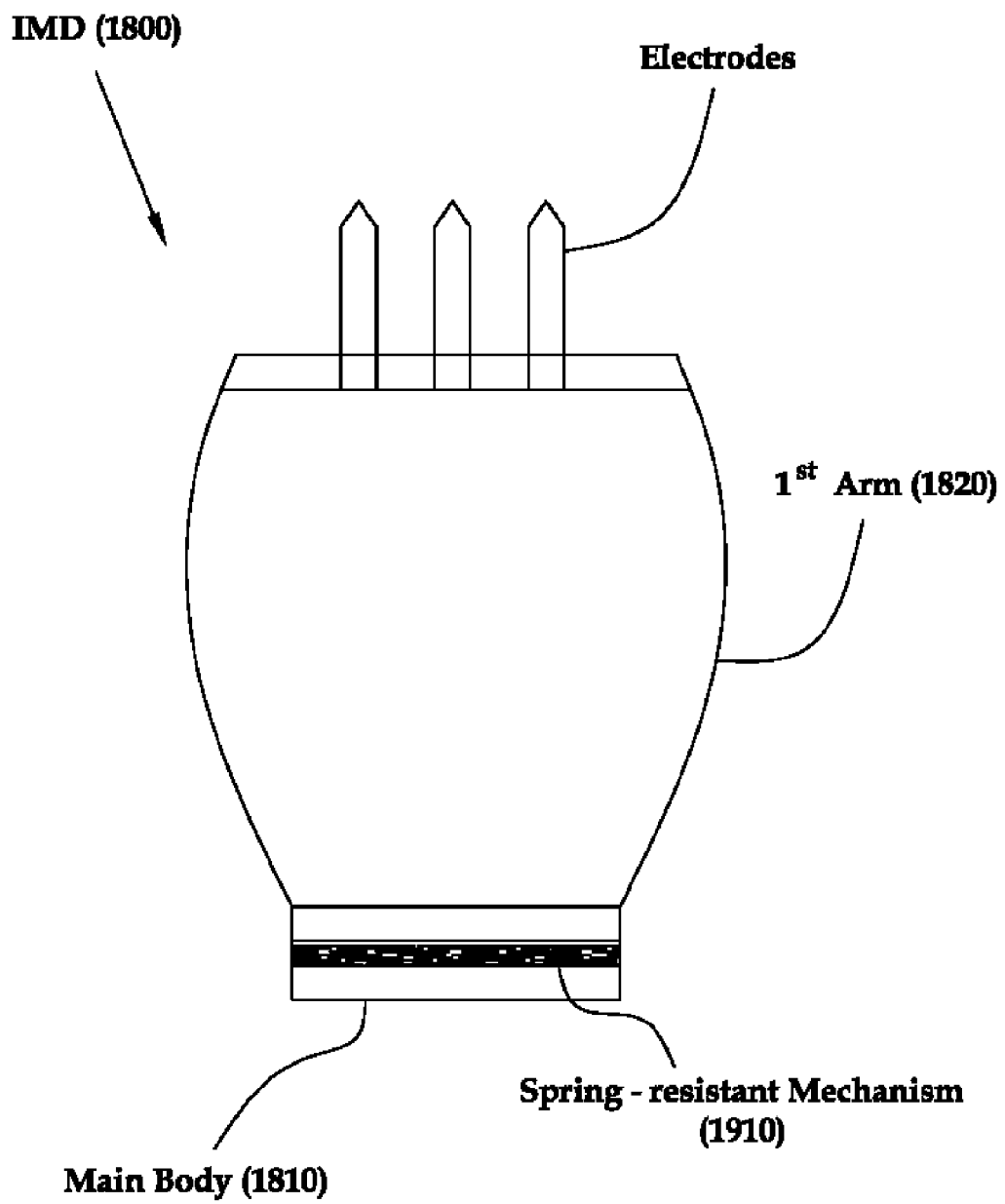
FIG. 19 illustrates a stylized side view of one portion of the IMD of FIG. 18.

FIG. 19 illustrates a stylized side view of one portion of the IMD 1800 of FIG. 18. The main body 1810 may comprise a spring mechanism 1910 (e.g., a spring clamping mechanism) and one or more components for delivering stimulation signals, i.e., similar to the components illustrated in the IMD 400 of FIG. 4. The spring mechanism 1910 provides for a "clamping" action that produces a force such that the electrodes may providing a clamping attachment to the inner lumen of the esophagus and stabilize the position of the IMD 1800. The arms 1820 may experience a force to secure or retain (i.e., retaining force) the IMD 1800 in a desired position. The arms 1820 may also consist of electronic devices such as one or more of the components illustrated in FIG. 4. The electrodes are capable of delivering electrical signal for providing stimulation of the vagus nerve.

Figure 20:
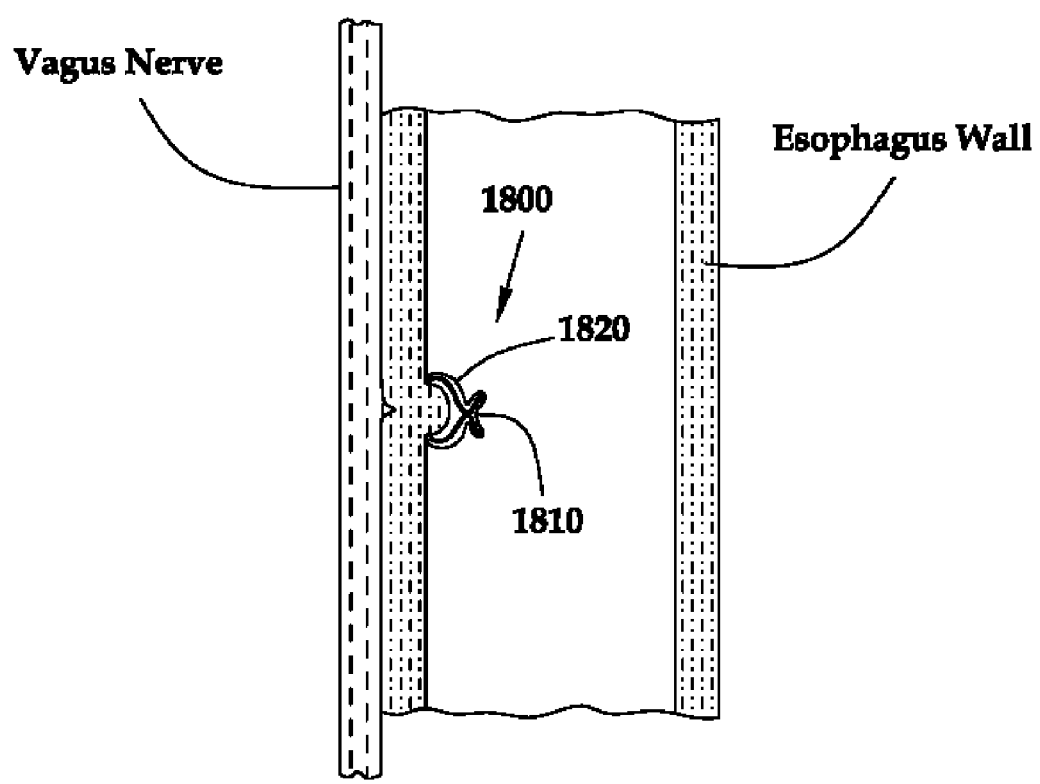
FIG. 20 illustrates a stylized depiction of the "clamping" action that results in a clamping of the electrodes of the IMD of FIG. 18 to the inner portion of the esophagus of the patient.

FIG. 20 illustrates a stylized depiction of the "clamping" action that results in the attachment the IMD 1800 to a portion of the inner lumen of the esophagus, in accordance with one embodiment of the present invention. The spring mechanism 1910 is capable of providing sufficient force to create a clamping or "pinching" action to also hold the IMD 1800 in place. This clamping action provides for contact of the tip electrodes with the inner lumen of the esophagus. Further, this pinching action provides for an inner surface of the clamped portion of the lumen to become in contact with the inner surface electrode 1830.

Figure 21:
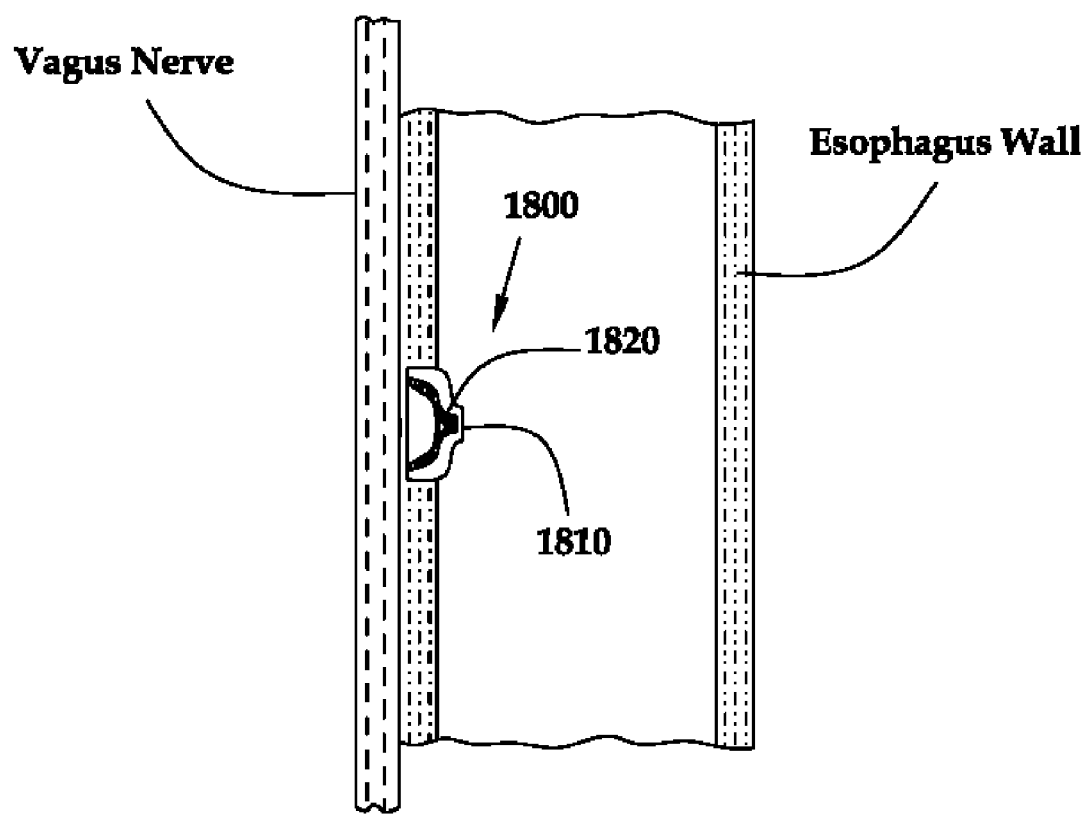
FIG. 21 illustrates a stylized depiction of the "clamping" action that results in a penetration of the tip electrodes of the IMD of FIG. 18 to the inner portion of the esophagus of the patient.

FIG. 21 illustrates a stylized depiction of the "clamping" action that results in the attachment the IMD 1800 to a portion of the inner lumen of the esophagus, in accordance with an alternative embodiment of the present invention. The spring mechanism 1910 is capable of providing sufficient force to not only penetrate the internal esophagus wall, but to also hold the IMD 1800 in place. The penetration of the tip electrodes 1840 provides for transmitting therapeutic electrical signals from a location in the abdominal esophagus that is more proximate to a portion of the vagus nerve. This may result in more efficient delivery therapeutic electrical signal from the IMD 1800 to a portion of the vagus nerve.

In one embodiment, the block diagram of the IMD 400 in FIG. 4 also represents the block diagram of the IMD 1800. In an alternative embodiment, the IMD 1800 may comprise the power supply 430 and the signal generation unit 420 for delivering an electrical signal for stimulating a portion of the vagus nerve. In this embodiment, the IMD 1800 may be a simple device capable of delivering pre-programmed stimulation signals to the inner esophagus wall and ultimately to a cranial nerve, such as the vagus nerve. In yet another alternative embodiment, the IMD 1800 may comprise power supply 430, the signal generation unit 420, and a communication coil 460 for receiving a programming signal from the external unit 120 for programming the IMD 1800 to generate with the desired therapeutic electrical signal.

Utilizing embodiments of the present invention, an efficient delivery of stimulation signals to a portion of the vagus nerve, may be performed. Further, in installing the IMD devices described herein into the esophagus provides for a less intrusive medical procedure. Access to the internal region of the esophagus may be gained using the technique illustrated in FIG. 8A. Therefore, in one embodiment, a non-surgical medical procedure would be sufficient to install the implantable medical devices illustrated in the embodiments of the present invention.

Further, certain side effects using conventional implantable medical devices may be reduced, such as a reduction in voice modulation, using embodiments of the present invention. Also, bi-lateral and/or unilateral stimulation may be provided by embodiments of the present invention. By employing alternating signals, bi-lateral stimulation of both vagus nerves (left vagus nerve and right vagus nerve) may be performed using the esophageal IMDs provided by embodiments of the present invention. Utilizing the embodiments of the present invention, a more direct access to the vagus nerve using non-surgical procedures may be realized. This may provide for more efficient usage of implantable medical devices for treating a plurality of medical disorders.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the methods described herein without departing from the concept, spirit and scope of the invention, as defined by the appended claims. It should be especially apparent that the principles of the invention may be applied to selected cranial nerves other than, or in addition to, the vagus nerve to achieve particular results in treating patients having epilepsy.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. An implantable medical device (IMD) for providing a trans-esophageal electrical signal to a target portion of the vagus nerve, comprising:
    a generally elongated outer shell comprising an upper surface configured in a generally convex shape, a lower surface opposite the upper surface, a leading end, and a trailing end opposite the leading end, wherein the leading end is substantially narrower than the trailing end, wherein the lower surface is configured in a generally flat shape for conforming to a portion of an inner wall of an esophagus of a patient, and wherein the outer shell is configured to be affixable to the inner wall of the esophagus with the substantially narrower leading end pointing up;

at least one electrode protruding from said outer shell and extending past the lower surface of the outer shell, said electrode capable of being electrically coupled to a portion of said inner wall of the esophagus of a patient;

a power supply to provide power for an operation performed by said IMD; and a signal generation unit operatively coupled to said power supply and to said at least one electrode, said signal generation unit to generate said electrical signal to provide a therapeutic electrical signal to a vagus nerve through at least a portion of the wall of the esophagus of said patient.

2. The implantable medical device of claim 1, wherein said outer shell comprises at least one suture structure selected from the group consisting of a suture hole and a suture loop, to allow for suturing said IMD to said inner wall of the esophagus.

3. The implantable medical device of claim 1, wherein said at least one electrode is formed as a hook capable of penetrating said inner wall of the esophagus for securing said IMD on said inner wall of the esophagus.

4. The implantable medical device of claim 1, wherein said IMD further comprises a communication unit for receiving a programming signal from an external unit for defining said electrical signal.

5. The implantable medical device claim 1, wherein said IMD further comprises a controller to control an operation of said medical device, and a magnetic field detection unit to receive a magnetic signal from an external source.

6. The implantable medical device claim 1, wherein at least one of the leading and trailing ends comprises a framed end configured with a low profile, and wherein said at least one framed end comprises a mechanism for securing said IMD onto said portion of said inner wall of the esophagus.

7. The IMD of claim 1, wherein the outer shell has a shape that allows food to travel down the esophagus past the IMD without excessive obstruction when the IMD is affixed to the inner wall of the esophagus with the substantially narrower leading end pointing up.

8. The IMD of claim 1, wherein the outer shell is generally leech shaped.

* * * * *